United States Patent
Moss et al.

(10) Patent No.: US 10,729,572 B2
(45) Date of Patent: Aug. 4, 2020

(54) METHODS AND DEVICES FOR DEPLOYING AND RELEASING A TEMPORARY IMPLANT WITHIN THE BODY

(71) Applicant: Allurion Technologies, Inc., Natick, MA (US)

(72) Inventors: Samuel Moss, Brookline, MA (US); Matthew S. Lake, Millis, MA (US); Jonathan Wecker, Weston, MA (US); Shantanu K. Gaur, Canonsburg, PA (US); Samuel G. Levy, Paris (FR); Bruce A. Horwitz, Newton, MA (US); Jinyoung Daniel Gwak, Palo Alto, CA (US)

(73) Assignee: Allurion Technologies, Inc., Natick, MA (US)

( * ) Notice: Subject to any disclaimer, the term of this patent is extended or adjusted under 35 U.S.C. 154(b) by 0 days.

(21) Appl. No.: 16/102,483

(22) Filed: Aug. 13, 2018

(65) Prior Publication Data
US 2018/0344498 A1    Dec. 6, 2018

Related U.S. Application Data

(63) Continuation of application No. 14/642,590, filed on Mar. 9, 2015, now Pat. No. 10,182,932, which is a continuation-in-part of application No. 14/069,776, filed on Nov. 1, 2013, now Pat. No. 8,974,483, which is a continuation-in-part of application No. 13/773,516, filed on Feb. 21, 2013, now Pat. No. 8,870,907.

(60) Provisional application No. 61/762,196, filed on Feb. 7, 2013, provisional application No. 61/601,384, filed on Feb. 21, 2012, provisional application No. 61/645,601, filed on May 10, 2012, provisional
(Continued)

(51) Int. Cl.
*A61F 5/00* (2006.01)
*A61M 39/22* (2006.01)

(52) U.S. Cl.
CPC ............ *A61F 5/003* (2013.01); *A61F 5/0036* (2013.01); *A61F 5/0046* (2013.01); *A61F 5/0089* (2013.01); *A61M 39/227* (2013.01)

(58) Field of Classification Search
CPC ...... A61F 5/0003; A61F 5/0013; A61F 5/003; A61F 5/0033; A61F 5/0036; A61F 5/0043; A61F 5/0073; A63H 27/10; A63H 2027/1041; A63H 2027/1083; A61M 39/24; A61M 2039/2433
USPC ........................................ 606/192; 623/23.65
See application file for complete search history.

(56) References Cited

U.S. PATENT DOCUMENTS

| 3,853,116 A | 12/1974 | Bucalo |
| 4,133,315 A | 1/1979 | Berman et al. |

(Continued)

FOREIGN PATENT DOCUMENTS

| CA | 2865056 | 8/2013 |
| CN | 201977967 | 9/2011 |

(Continued)

*Primary Examiner* — Martin T Ton
(74) *Attorney, Agent, or Firm* — Levine Bagade Han LLP

(57) ABSTRACT

Methods, devices and systems for delivering a device assembly into a gastric or other space within the body, allowing the device to expand to occupy volume within the gastric space and, after an effective period of time, delivering a substance or stimulus to begin breakdown of the expanded device so that it may release from the body.

19 Claims, 21 Drawing Sheets

Related U.S. Application Data application No. 61/647,730, filed on May 16, 2012, provisional application No. 61/663,433, filed on Jun. 22, 2012, provisional application No. 61/663,682, filed on Jun. 25, 2012, provisional application No. 61/663,683, filed on Jun. 25, 2012, provisional application No. 61/674,126, filed on Jul. 20, 2012, provisional application No. 61/699,942, filed on Sep. 12, 2012.

(56) References Cited

U.S. PATENT DOCUMENTS

| | | |
|---|---|---|
| 4,141,771 A | 2/1979 | Barker et al. |
| 4,370,374 A | 1/1983 | Raabe et al. |
| 4,723,547 A | 2/1988 | Kullas et al. |
| 4,842,007 A * | 6/1989 | Kurtz ............... A63H 27/10 137/223 |
| 4,899,747 A | 2/1990 | Garren et al. |
| 4,949,756 A | 8/1990 | Melinyshyn et al. |
| 5,181,921 A | 1/1993 | Makita et al. |
| 5,336,123 A | 8/1994 | Laske et al. |
| 5,348,537 A | 9/1994 | Wiesner et al. |
| 5,496,203 A * | 3/1996 | Murray ............... A63H 27/10 446/221 |
| 5,595,521 A | 1/1997 | Becker |
| 5,950,624 A | 9/1999 | Hart |
| 6,259,953 B1 | 7/2001 | Lucchesi et al. |
| 6,375,972 B1 | 4/2002 | Guo et al. |
| 6,460,541 B1 | 10/2002 | Shah et al. |
| 6,712,832 B2 | 3/2004 | Shah |
| 6,939,292 B2 | 9/2005 | Mizuno et al. |
| 7,172,613 B2 | 2/2007 | Wazne |
| 7,485,093 B2 | 2/2009 | Glukhovsky |
| 7,854,745 B2 | 12/2010 | Brister et al. |
| 8,183,227 B1 | 5/2012 | Perrin et al. |
| 8,202,291 B1 | 6/2012 | Brister et al. |
| 8,287,562 B2 | 10/2012 | Kasic, II |
| 8,292,911 B2 | 10/2012 | Brister et al. |
| 8,585,676 B2 | 11/2013 | Shah |
| 8,740,845 B2 | 6/2014 | Shah et al. |
| 8,814,898 B2 | 8/2014 | Gaur et al. |
| 8,870,907 B2 | 10/2014 | Gaur et al. |
| 8,974,483 B2 | 3/2015 | Gaur et al. |
| 9,387,107 B2 | 7/2016 | Gaur et al. |
| 9,662,239 B2 | 5/2017 | Brister et al. |
| 9,827,129 B2 | 11/2017 | Gaur et al. |
| 9,849,018 B2 | 12/2017 | Wecker et al. |
| 10,182,932 B2 | 1/2019 | Moss et al. |
| 10,307,279 B2 | 6/2019 | Wecker et al. |
| 2002/0198470 A1 | 12/2002 | Imran et al. |
| 2003/0229263 A1 | 12/2003 | Connors et al. |
| 2003/0229384 A1 | 12/2003 | Mon |
| 2004/0101540 A1 | 5/2004 | Cooker |
| 2004/0146559 A1 | 7/2004 | Sowden et al. |
| 2005/0055039 A1 | 3/2005 | Burnett et al. |
| 2006/0222705 A1 | 10/2006 | Flanner et al. |
| 2007/0010791 A1 | 1/2007 | Drechsler et al. |
| 2007/0078476 A1 | 4/2007 | Hull, Sr. et al. |
| 2008/0195226 A1 | 8/2008 | Williams et al. |
| 2008/0241094 A1 | 10/2008 | Burnett et al. |
| 2008/0243071 A1 | 10/2008 | Quijano et al. |
| 2008/0249635 A1 | 10/2008 | Weitzner et al. |
| 2008/0269555 A1 | 10/2008 | Paganon et al. |
| 2009/0024227 A1 | 1/2009 | Lesh |
| 2009/0048684 A1 | 2/2009 | Lesh |
| 2009/0118756 A1 | 5/2009 | Valencon |
| 2009/0192535 A1 | 7/2009 | Kasic |
| 2009/0259246 A1 | 10/2009 | Eskaros et al. |
| 2009/0299327 A1 | 12/2009 | Tilson et al. |
| 2010/0062057 A1 | 3/2010 | Berge et al. |
| 2010/0100116 A1 | 4/2010 | Brister et al. |
| 2010/0121224 A1 | 5/2010 | Toyota et al. |
| 2010/0137897 A1 * | 6/2010 | Brister ............... A61F 5/003 606/192 |
| 2010/0174307 A1 | 7/2010 | Birk |
| 2010/0246165 A1 * | 9/2010 | Diaz ............... A63H 27/10 362/183 |
| 2010/0274194 A1 | 10/2010 | Sobelman et al. |
| 2011/0004236 A1 | 1/2011 | Priplata et al. |
| 2011/0112383 A1 | 5/2011 | Voss et al. |
| 2012/0141544 A1 | 6/2012 | Fuisz et al. |
| 2012/0141545 A1 | 6/2012 | Fuisz et al. |
| 2012/0232576 A1 | 9/2012 | Brister et al. |
| 2013/0035711 A1 | 2/2013 | Schwab et al. |
| 2013/0190796 A1 | 7/2013 | Tilson et al. |
| 2013/0218190 A1 | 8/2013 | Gaur et al. |
| 2013/0267984 A1 | 10/2013 | Gaur et al. |
| 2013/0296751 A1 | 11/2013 | Martin et al. |
| 2014/0066967 A1 | 3/2014 | Levy et al. |
| 2014/0188151 A1 | 7/2014 | Gaur et al. |
| 2014/0296903 A1 | 10/2014 | Gaur et al. |
| 2015/0196408 A1 | 7/2015 | Moss et al. |
| 2016/0278957 A1 | 9/2016 | Gaur et al. |
| 2018/0042747 A1 | 2/2018 | Gaur et al. |
| 2018/0071127 A1 | 3/2018 | Wecker et al. |
| 2018/0311484 A1 | 11/2018 | Lake et al. |

FOREIGN PATENT DOCUMENTS

| | | |
|---|---|---|
| EP | 2817062 | 12/2014 |
| JP | 2008-513132 | 5/2008 |
| JP | 2008-515464 | 5/2008 |
| JP | 2010-523280 | 7/2010 |
| JP | 2011-517611 | 6/2011 |
| WO | WO 2000/012167 | 3/2000 |
| WO | WO 2006/020929 | 2/2006 |
| WO | WO 2009/059802 | 5/2009 |
| WO | WO 2011/106157 | 9/2011 |
| WO | WO 2013/126593 | 8/2013 |
| WO | WO 2014/074625 | 5/2014 |
| WO | WO 2015/066545 | 5/2015 |
| WO | WO 2016/145076 | 9/2016 |
| WO | WO 2017/136840 | 8/2017 |

* cited by examiner

METHODS AND DEVICES FOR DEPLOYING AND RELEASING A TEMPORARY IMPLANT WITHIN THE BODY

CROSS-REFERENCE TO RELATED APPLICATIONS

This application is a continuation of U.S. patent application Ser. No. 14/642,590 filed Mar. 9, 2015, which is a continuation-in-part of U.S. patent application Ser. No. 14/069,776 filed Nov. 1, 2013 (now U.S. Pat. No. 8,974,483) entitled Methods and Devices for Deploying and Releasing a Temporary Implant Within the Body, which is a continuation-in-part of U.S. patent application Ser. No. 13/773,516 filed Feb. 21, 2013 (now U.S. Pat. No. 8,870,907 issued Oct. 28, 2014), which is a non-provisional of U.S. Provisional Applications No. 61/762,196 entitled Thermally Degradable Biocompatible Constructs and Methods of Degrading filed Feb. 7, 2013; 61/601,384 entitled Swallowed Intragastric Balloon Filled via Narrow Extracorporeal Tube filed Feb. 21, 2012; 61/645,601 entitled Delivery String for Gastrointestinal Applications filed May 10, 2012; 61/647,730 entitled Hydrogel Driven Valve filed May 16, 2012; 61/663,433 entitled Fluid Transfer Device for Hydrogel Constructs filed Jun. 22, 2012; 61/663,682 entitled Hydrogel Driven Valve filed Jun. 25, 2012; 61/663,683 entitled Fluid Transfer Device for Hydrogel Constructs filed Jun. 25, 2012; No. 61/674,126 entitled Payload Delivery System and Method filed Jul. 20, 2012; and 61/699,942 entitled System for Rapid Hydrogel Construct Degradation filed Sep. 12, 2012, the entirety of each of which is incorporated by reference.

BACKGROUND OF THE INVENTION

The present invention generally relates to the field of devices that temporarily occlude spaces within the body to provide a therapeutic effect.

According to 2010 World Health Organization data, 198 million Americans over the age of 15 are above target weight. Of these individuals, 89 million are considered overweight (25<Body Mass Index<30) and 109 million are considered obese (Body Mass Index>30). Worldwide, more than 1.4 billion adults age 20 and over are overweight, and 500 million are obese. Obesity places patients at increased risk of numerous, potentially disabling conditions including type 2 diabetes, heart disease, stroke, gallbladder disease, and musculoskeletal disorders 1, 2, 3. Compared with healthy weight adults, obese adults are more than three times as likely to have been diagnosed with diabetes or high blood pressure 4. In the United States it is estimated that one in five cancer-related deaths may be attributable to obesity in female non-smokers and one in seven among male non-smokers (>=50 years of age). On average, men and women who were obese at age 40 live 5.8 and 7.1 fewer years, respectively, than their healthy weight peers.

Gastric bypass surgery is the current gold standard treatment for patients with a body mass index ("BMI") of greater than 40. Gastric bypass surgery is also an option for those with a BMI between 35-39 with obesity-related co-morbidities. While gastric bypass surgery results in decreased food consumption and weight loss for a majority of recipients, it requires life-altering, permanent anatomic modifications to the gastrointestinal tract and can result in severe complications. Gastric bypass and related surgical procedures are also expensive, costing about 22,500 (by laparoscopy). For these reasons, only about 250,000 surgical obesity procedures are performed per year in the US.

For the vast majority of the overweight and obese population for whom surgical obesity procedures are not appropriate, few efficacious and affordable interventions are currently available. Diet and exercise remain the front line approaches to obesity, however this approach has at best slowed the growth of the epidemic. To date, drug therapies have dose limiting side effects or have lacked meaningful long term efficacy.

One less-invasive intervention that has begun to gain popularity is an intragastric balloon. Intragastric balloons can be placed endoscopically or positioned using other methods and generally must be removed endoscopically or rely on the body's natural digestive processes for removal.

The devices, methods, and systems discussed herein are intended to provide an effective treatment for obesity. Moreover, the devices, methods, and systems described herein are not limited to any particular patient population and can even be applied to clinical areas outside of obesity.

SUMMARY OF THE INVENTION

The present invention relates to devices and methods for occupying a space within a patient's body. In particular, the devices and methods can be used within a gastric space. However, the devices and methods can be used in any part of the body.

The devices described herein can also be used for delivery of drugs, pharmaceuticals, or other agents where such items can be delivered on a skin of the device, within a reservoir, in a filler of the device, or anywhere on the device. Such agents can be released over time.

The present disclosure includes medical devices for use with a liquid filler material and for occupying a space within the patient's body. In one example, the medical device is a device for occupying a space within a patient's body and for use with a fluid delivery conduit that allows transport of a fluid into the medical device. For example, such a device can include a device body defining an reservoir; a tunnel member having an elongate flattened shape, the tunnel member comprising a first open end located within the reservoir and a second open end located exterior to the reservoir, the tunnel member having at least two interior opposing surfaces that define a tunnel lumen extending longitudinally between the first open end and the second open end; and where the tunnel lumen is sized to slidably receive the fluid delivery conduit within the second open end such that the fluid delivery conduit separates the interior opposing surfaces deforming the elongate flattened shape to an elongated expanded shape; wherein removal of the fluid delivery member causes the tunnel member to revert to the elongate flattened shape such that the interior opposing surfaces move together to narrow the tunnel lumen and increase a resistance to fluid flow through the tunnel lumen.

In one example, the tunnel member comprises a flexible thin wall material such that the lumen can self-close to prevent fluid flowing therethrough when the fluid delivery conduit is removed therefrom. In additional variations, the increasing pressure within the reservoir caused by addition of a liquid or gas increases the resistance to fluid flow through the tunnel lumen.

In an additional variation, the medical device further comprises a substance within the tunnel member that increases the resistance to fluid flow through the tunnel lumen upon removal of the fluid delivery conduit. Such a substance can be a hygroscopic material, a material swells upon contact with the patients bodily fluids or a liquid within the reservoir, a low-solubility material, a bio-compatible lubricant, and/or a viscous material where after removal of the fluid delivery member a cohesion of the viscous material increases a force required to separate the interior opposing surfaces.

The tunnel member can include a first layer and a second layer sealed along at least a first longitudinal edge, the tunnel lumen being adjacent to the longitudinal edge. In an additional variation, the tunnel includes a second longitudinal edge adjacent to the tunnel lumen and opposite to the first longitudinal edge, where the first layer and second layer are sealed along the second longitudinal edge.

Variations of the device include a mechanical attachment coupling the fluid delivery member to a portion of the tunnel member. The mechanical attachment can comprise a suture, and/or a mechanical or chemical bond.

In some variations, a diameter of the tunnel lumen is constant. In alternate variations, the diameter of the tunnel lumen varies within the tunnel member. Additional variations include a tunnel member having at least one pocket in fluid communication with the tunnel lumen where the at least one pocket is configured to retain a substance therein.

The second open end of the tunnel member can be at least even with an outer perimeter of the device body. Alternatively, or in combination, the tunnel member comprises a detachable section having a reduced tensile strength region, such that application of a tensile force causes detachment of the detachable section.

The present disclosure also includes variations of medical devices for occupying a space within a patient's body. In one such example, such a medical device includes a device body defining an reservoir; a fluid delivery conduit that allows transport of a fluid into the reservoir; a tunnel member having an elongate flattened shape, the tunnel member comprising a first open end located within the reservoir and a second open end located exterior to the reservoir, the tunnel member having at least two interior opposing surfaces that define a tunnel lumen extending longitudinally between the first open end and the second open end; and where the tunnel lumen is sized to slidably receive the fluid delivery conduit within the second open end such that the fluid delivery conduit separates the interior opposing surfaces deforming the elongate flattened shape to an elongated expanded shape; wherein removal of the fluid delivery member causes the tunnel member to revert to the elongate flattened shape such that the interior opposing surfaces move together to narrow the tunnel lumen and increase a resistance to fluid flow through the tunnel lumen.

In another variation, a device can include a medical device for occupying a space within a patient's body and for use with a fluid delivery conduit that allows transport of a fluid into the medical device, the medical device comprising: a device body defining an reservoir; a fluid valve having an elongate flattened shape, the fluid valve comprising an internal open end located within the reservoir and an external open end located exterior to the reservoir, the fluid valve having an elongate flattened passage extending longitudinally between the external open end and the internal open end, where the flattened passage is defined by at least two opposing segments of a fluid impermeable interior surface, where the elongate flattened passage includes a lumen extending therethrough such that the lumen remains occluded until separation of the at least two opposing segments; and where the passage is sized to slidably receive the fluid delivery conduit within the external open end such that the fluid delivery conduit separates the interior opposing segments deforming the elongate flattened shape into the elongated lumen; wherein removal of the fluid delivery conduit causes the fluid valve to revert to the elongate flattened shape such that the interior opposing segments move together to narrow the lumen and increase a resistance to fluid flow through the lumen.

A variation of the fluid valve can include a flexible thin wall material such that increasing a pressure within the reservoir increases the resistance to fluid flow through the tunnel lumen. The fluid valve can include a substance within the fluid valve wherein the substance increases the resistance to fluid flow through the tunnel lumen upon removal of the fluid delivery conduit.

The substance can comprise a viscous material such that after removal of the fluid delivery conduit a cohesion of the viscous material increases a force required to separate the interior opposing segments.

The fluid valve can include a detachable section having a reduced tensile strength region, such that application of a tensile force causes detachment of the detachable section. The fluid valve can also be attached to an interior surface of the device body.

The present disclosure also includes a fluid fill valve for use with a medical device for occupying a space within a patient's body and for use with a fluid delivery conduit. In one example such a valve includes a first layer of fluid impermeable membrane and a second layer of fluid impermeable membrane, wherein a portion of the layers are sealingly joined to form a valve body, the valve body having an internal end disposed inside the device and an external end external to or at the surface of the device; and wherein the first layer and second layer include an unsealed region that forms a lumen region longitudinally extending in the valve body from the internal end to the external end; where the first layer and second layer are configured to join together in the lumen region reducing a diameter of the lumen region to resist passage fluids therethrough, where the lumen region is configured to permit advancement of the fluid delivery conduit therethrough.

In one variation of the valve the first fluid impermeable membrane has a length and a width and two lengthwise edges and where the second fluid impermeable membrane has a length and a width and two lengthwise edges, the length and width being substantially the same as the first fluid impermeable membrane.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention. In addition, aspects of the variations, as well as the variations themselves can be combined such that the combination is within the scope of this disclosure.

BRIEF DESCRIPTION OF THE DRAWINGS

The foregoing and other objects, features and advantages of the methods, devices, and systems described herein will become apparent from the following description in conjunction with the accompanying drawings, in which reference characters refer to the same parts throughout the different views. The drawings are not necessarily to scale; emphasis has instead been placed upon illustrating the principles of the invention. Of the drawings.

DETAILED DESCRIPTION OF THE INVENTION

The following illustrations are examples of the invention described herein. It is contemplated that combinations of aspects of specific embodiments or combinations of the specific embodiments themselves are within the scope of this disclosure. While the methods, devices, and systems described herein are discussed as being used in the stomach or gastric space, the devices, methods, and systems of the present disclosure can be can be used in other parts of the body where temporary occlusion of a space might be required or beneficial. The present disclosure is related to commonly assigned to US Publication No. 2011/0295299 filed Mar. 2, 2011, the entirety of which is incorporated by reference.

Figure 1A:
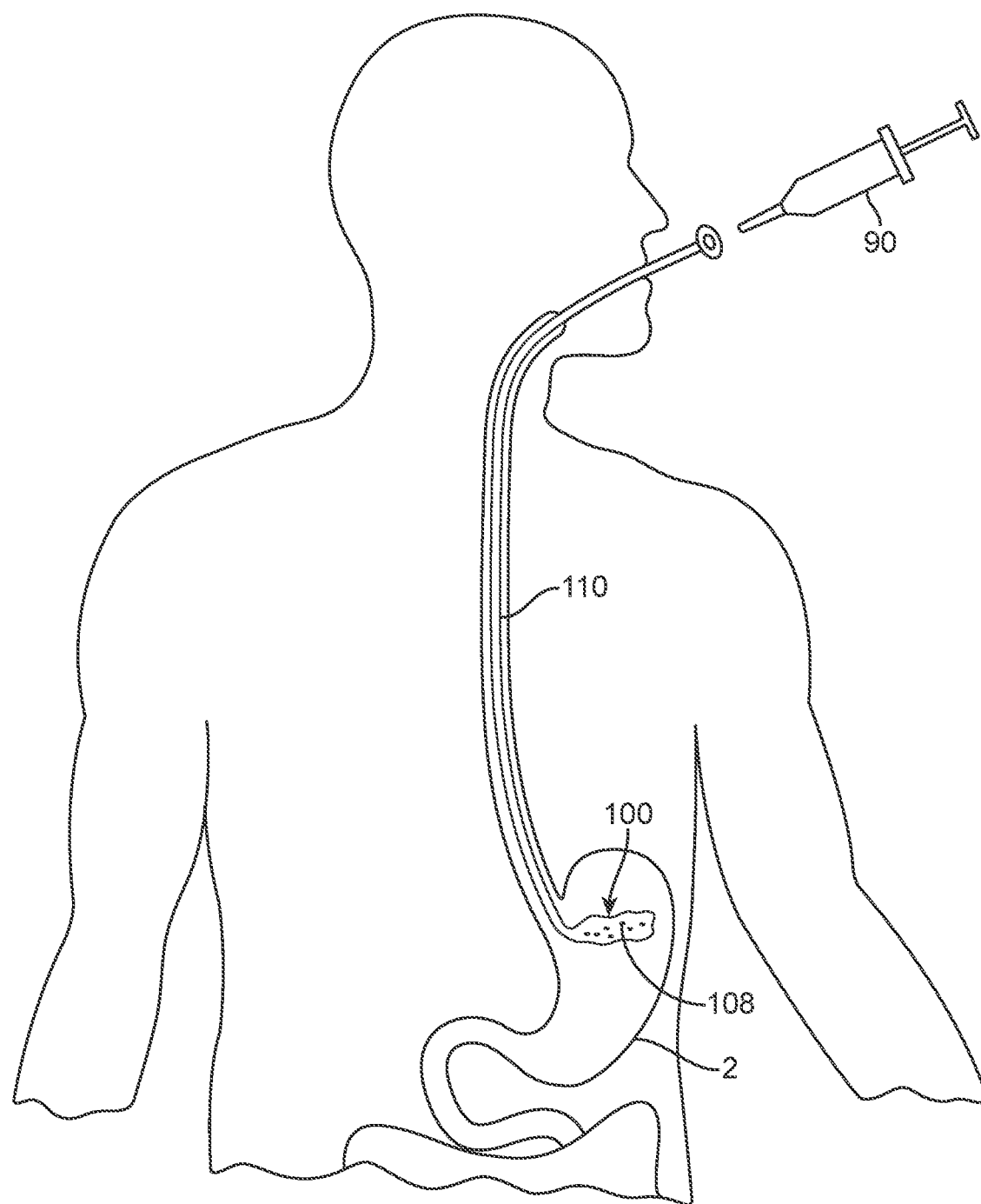
FIG. 1A, illustrates an example of a gastric device assembly prior to assuming an active profile.

FIG. 1A, illustrates an example of a gastric device assembly 100. In this example, the gastric device assembly or construct 100 can reside in a stomach (typically of a mammal) for an extended period of time. One benefit of such a device is that, when partially or fully deployed, the construct 100 occupies volume within the stomach to produce a therapeutic effect, e.g., to stimulate the sensation of satiety, and resists passage from the body by normal body function. As illustrated below the construct generally comprises three states: a pre-deployment configuration (FIG. 1A); a deployed or active configuration (FIG. 1D, 1E); and a release configuration (FIG. 1F). As noted above, the device can also be used for therapeutic benefits that do not involve occupying volume (e.g., drug delivery, creation of a cavity by separating adjacent tissue, etc.).

FIG. 1A illustrates a variation of the device 100 after placement within a stomach 2. As described herein, the initial configuration of the device 100 includes a compact state that allows placement within the body. The device can be in a pill-type configuration or any other shape that permits swallowing. Alternatively, the device 100 can be positioned by the use of a scope type device, catheter, or other medical positioning device.

For a device used in the digestive tract/gastric space, the device assembly 100 can be positioned within the body either by natural ingestion or the use of a delivery system (such as a catheter, endoscope, or other medical device). The delivery system can optionally comprise an oral dosage form, not illustrated, which facilitates the ingestion of a relatively large object. In other embodiments the system comprises a tether that allows manipulation or control of the placed construct from outside of the body. The assembly 100 can also be placed in the stomach by more invasive surgical or endoscopic procedures.

In FIG. 1A, the device 100 is shown immediately after being deployed within the stomach 2 and is ready to be activated. As noted herein, the device 100 can be deployed in the configuration shown. Alternatively, the device can be contained within a capsule or pill-type casing that allows for swallowing by a patient. Once swallowed, the casing will readily dissolve or break down resulting in the configuration shown. Once in place in the stomach, the assembly 100 begins to expand in order to occupy volume/space within the body. Expansion can occur via manual inflation, including hydration or other activation of a filler material (as shown optionally using a catheter, inflation tube or other delivery system), via absorption of body fluids, via remote actuation of a substance already located within the device assembly, and/or delivering of a fluid into the assembly, where the fluid itself causes expansion. Variations of the device also include a combination of such expansion means.

The variation shown in FIG. 1A includes a member 110 that extends from the device 100 to outside of the patient. In this variation shown, the member 110 comprises a fluid transport member that is fluidly coupled to an interior of the device 100 allowing for the delivery of substances and/or fluids within the device 100. FIG. 1A shows an exemplary fluid source 90 coupleable to a variation of a fluid transport member 110 such that the delivery of fluid causes a filler material 108 within the device to expand. In the illustrated example, the fluid transport member comprises a conduit. However, alternate variations of the devices described herein include fluid transport members that reside within the patient's body. Alternate variations of the device 100 also include members 110 that function as delivery or positioning systems to ensure proper placement of the device 100 within the body. Such delivery systems may or may not be fluidly coupled with an interior of the device. In variations discussed below, the device can include one or more fluid transport members that remain within the body but still convey fluid into the device 100 to allow the device to assume an active profile.

Figure 1B:
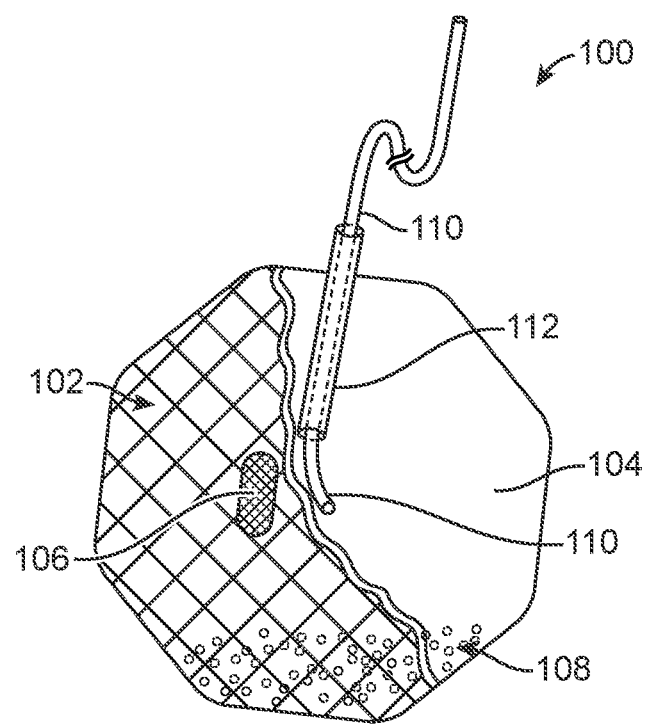
FIGS. 1B and 1C show partial cutaway views of examples of device assemblies for use in occupying space within a body.

FIG. 1B shows one a partial cutaway view of an example of a device assembly 100 for use in occupying space within a body. In this variation, the device assembly 100 includes a material surface or skin 102 that forms a reservoir or pocket 104 capable of retaining a variety of substances, including but not limited to fluids, solid substances, semi-solid substances, etc. In the illustrated variation, the reservoir 104 holds a filler material 108 such as dehydrated hydrogel granules that can swell in size upon the addition of a fluid. However, any number of substances can be contained within the reservoir 104. Alternate variations of the device and/or method include assemblies that do not include a filler material; rather a filler material can be deposited within the reservoir 104 once the assembly is deployed. Alternatively, or in combination, the reservoir can be filled with a gas, liquid or other gel type substance.

In other variations, the device assembly 100 can include an empty reservoir that can be deployed into the body and subsequently filled with a filler material or other substance. For example, such variations can include a liquid filler material that is delivered to the reservoir through a conduit. The volume of liquid required to expand the device into a desired active profile can pre-determined. In some variations, the volume can be determined by measuring the back pressure in the conduit or pressure within the reservoir using any number of pressure detecting elements.

FIG. 1B also illustrates a variation of a sealable fluid path 112 coupled to and/or forming part of the fluid transfer member. In this example, the sealable fluid path 112 extends outside of the perimeter of the skin 102 of the device 100. Additional variations of the device 100 can include significantly shortened sealable fluid paths 112. In yet additional variations, the device assembly 100 can omit the sealable fluid path 112.

As noted herein, the skin 102 includes a release material 106 coupled thereto, where the release material 106 allows for initiating release of the assembly 100 from the body shortly after degradation, activation, or breakdown of the release material. Once the device assembly 100 is in the active profile, it can remain in the active profile for a pre-determined amount of time or until the patient experiences a desired therapeutic effect. To initiate release of the device assembly 100 from the body, an exogenous material, substance or stimulus is administered to the patient. The substance can comprise a fluid or other activating agent having properties that either directly or indirectly act on the release material to disrupt the barrier and allow the contents of the reservoir to be exposed to the body. For example, the exogenous substance can comprise a heated fluid that melts the release material. Alternatively, the exogenous material can change a temperature and/or an acidity of fluids in the stomach such that the enhanced properties of the fluids begin to act, either directly or indirectly, upon the release materials. In additional variations, the release material can comprise a material or materials that effectively form a barrier as discussed herein and are separated or disengaged by the use of an exogenous stimuli (e.g., a magnetic field, ultrasound, IR heating, coherent light, electromagnetic signals, microwave field, etc.).

FIG. 1B also illustrates a variation where the release material 106 is in the form that approximates shape and/or size of the casing used to deliver the device 100 (in this example the release material 106 is in a pill shape). One benefit of such a configuration is that the release material 106 can be positioned within the casing without excessive folding or bending.

Figure 1C:
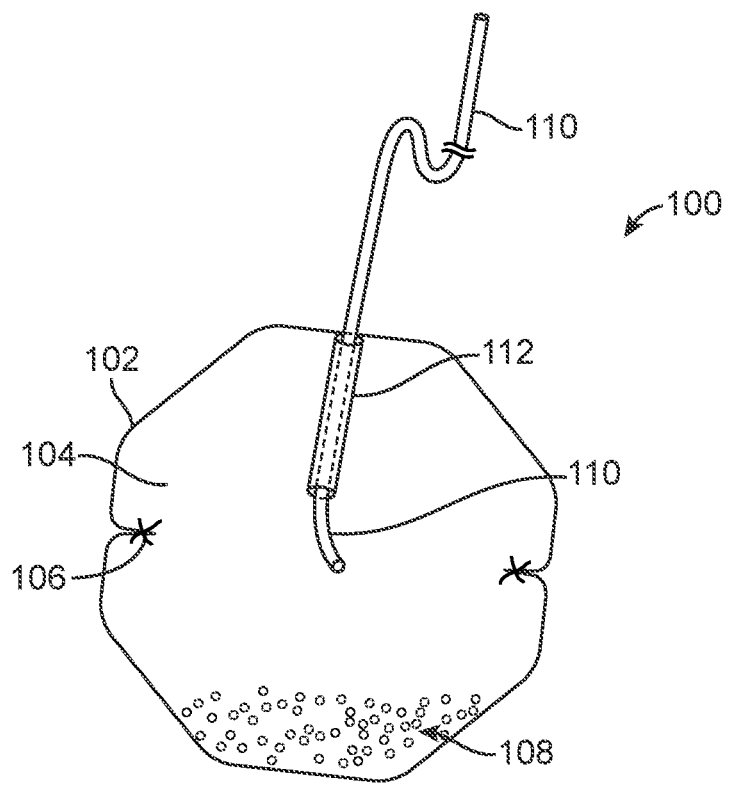

FIG. 1C illustrates a sectional view of another variation of a device assembly 100. In this variation, the release material 106 binds or otherwise joins edges of the skin from within the reservoir 104. Such a configuration protects the release material 106 from the local environment of the body (e.g., fluids within the stomach or digestive tract). The release material can still be activated and/or degraded by the addition of the exogenous material to the body as described herein. However, positioning of the release material within the reservoir permits the skin 102 to serve as an additional layer of protection to prevent inadvertent release of the device assembly 100. The release material 106 can comprise a layer that binds edges of the skin together.

FIG. 1C also illustrates a variation of a sealable fluid path 112. In this example, the sealable fluid path 112 does not extend outside of the perimeter of the skin 102. Additional variations of the device 100 can include significantly shortened sealable fluid paths 112. In yet additional variations, the device assembly 100 can omit the sealable fluid path 112.

Figure 1D:
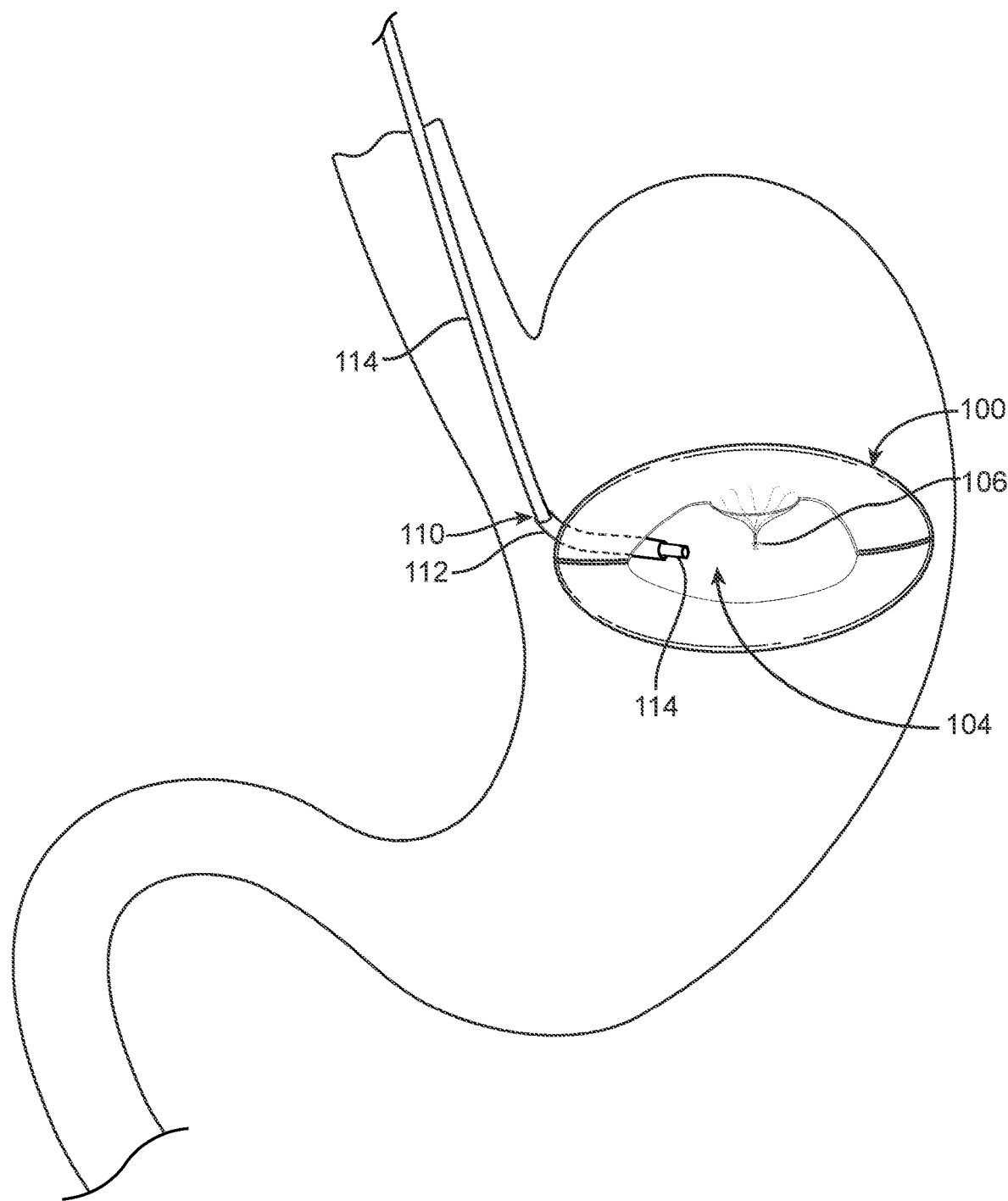
FIG. 1D illustrates the variation of the device shown in FIG. 1A as the device assembly assumes an active profile.

FIG. 1D illustrates the variation of the device 100 shown in FIG. 1A as the device assembly 100 assumes an active profile. In this example, the device 100 does not include a filler material 108 as depicted in FIG. 1C, instead, the filler material can comprise a liquid, gas, gel, or other substance that is delivered through the conduit 114 and/or sealable fluid path 112. An active profile includes any profile apart from a deployment state and where the profile allows the device to perform the intended effect of occupying volume or space within the body to produce a therapeutic effect. In the illustrated example, a physician or other medical practitioner delivers fluid via the fluid transport member 110, comprising a conduit 114 in this variation, and into the reservoir 104. As noted herein, other variations include device assemblies with a filler material where the conduit 114 simply delivers fluid, causing the filler material 108 to swell to achieve an active profile.

When using a conduit 114 that extends outside of the body, a physician can deliver a hydrating liquid, such as water or distilled water through the conduit 114. Generally, a pre-determined volume of liquid can be manually or mechanically pumped into the exterior end of the conduit wherein the volume of liquid is pre-determined based on a particular size of the device assembly or based on a desired active state. In some variations, the volume of liquid can also depend on the length of conduit.

The conduit 114 can be used to transfer a substance or into the reservoir 104 of the device. In the illustrated variation, the conduit 114 transfers fluid from outside of the patient's body into the reservoir 104 after deployment of device assembly 100 within the body. Alternatively, or in combination, a fluid transfer member can comprise a wick type device that transfers liquids or other fluids from within the body to the reservoir.

Figure 1E:
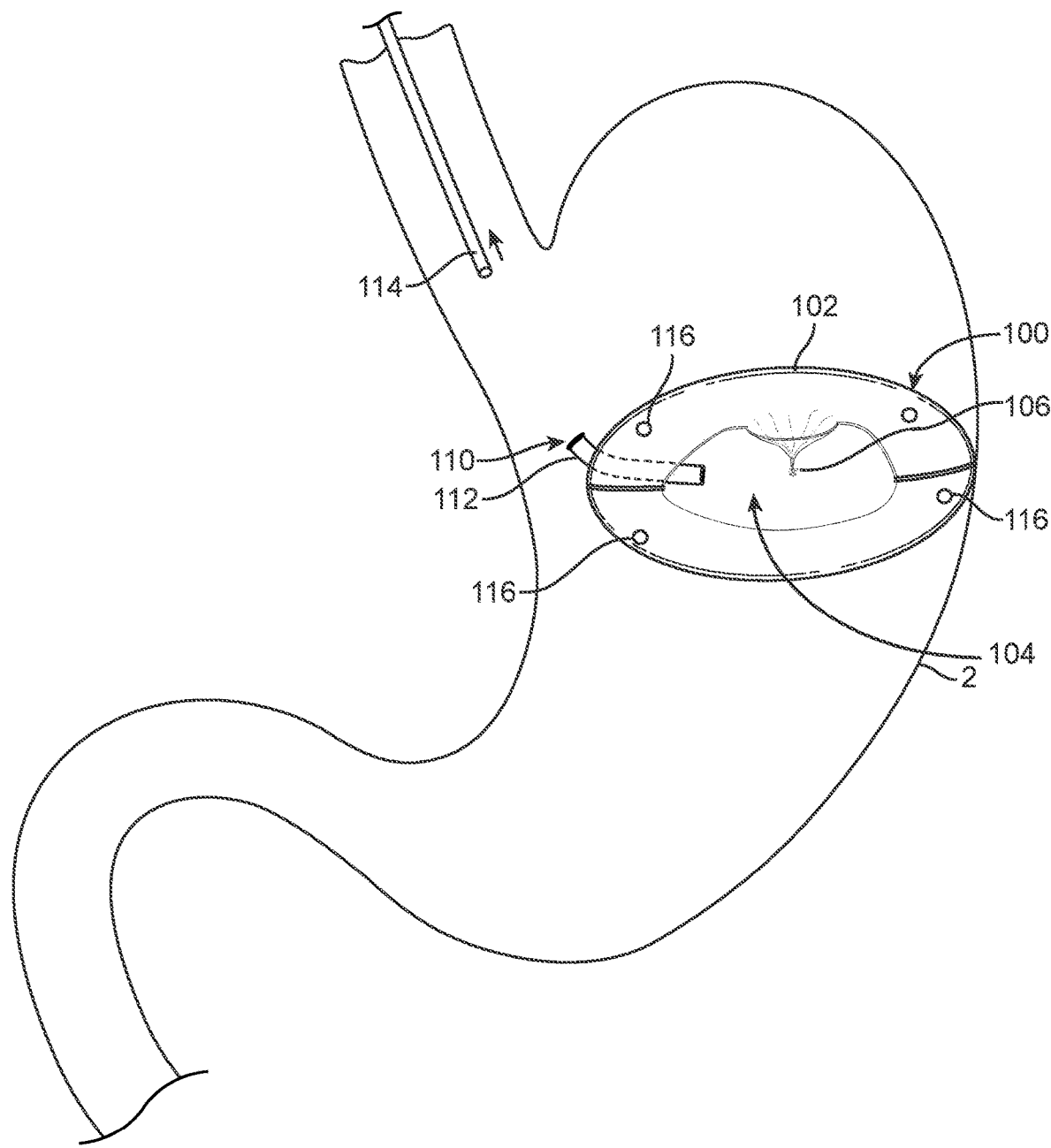
FIG. 1E shows a device assembly after it is inflated, expanded, or otherwise transitioned to achieve a desired active profile.
Figure 1F:
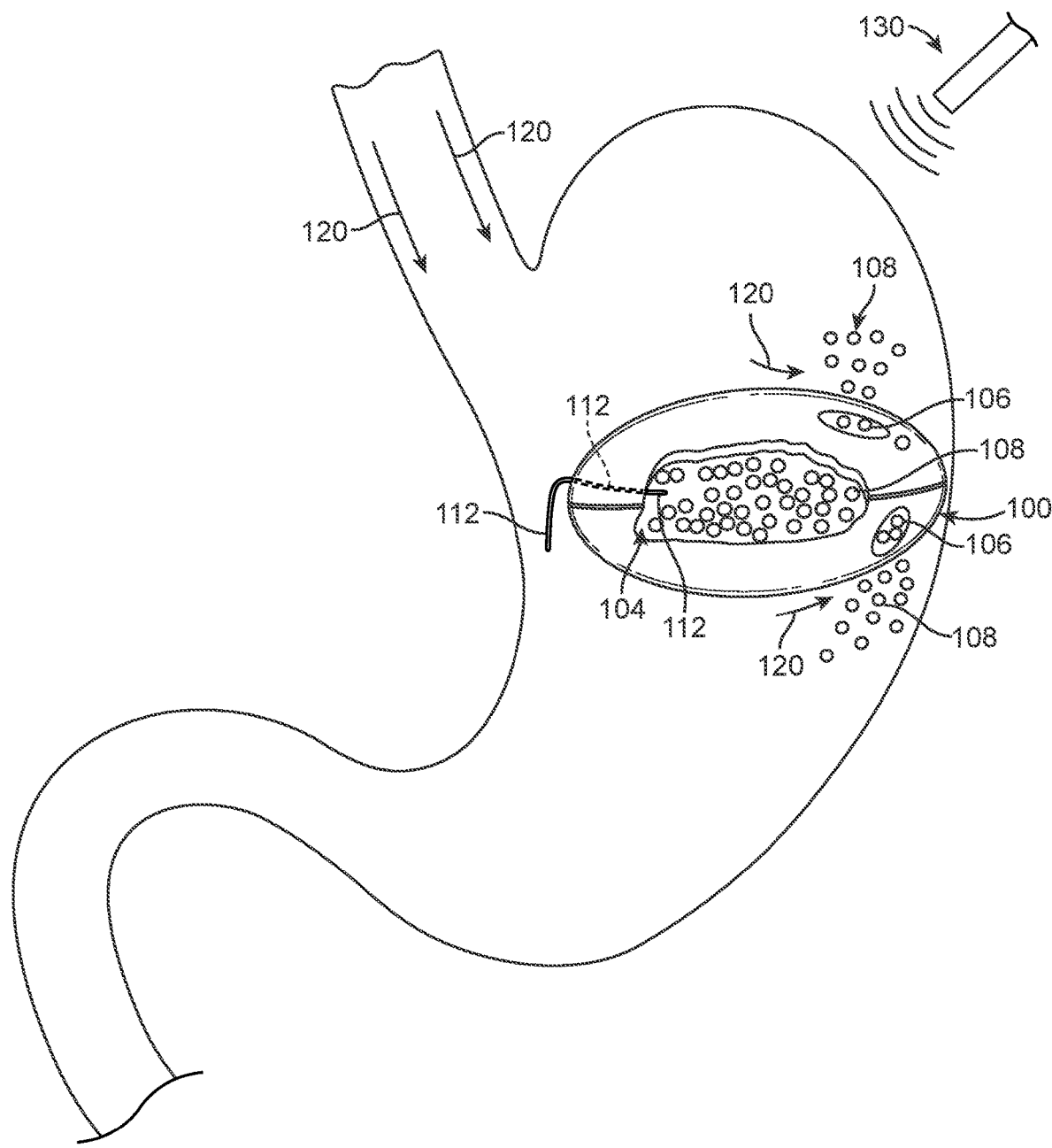
FIG. 1F illustrates a state of a device assembly after a physician, patient, or other caregiver desires to initiate release the device assembly from the body.

FIG. 1E shows the device assembly 100 after it is inflated, expanded, or otherwise transitioned to achieve a desired active profile. A physician can monitor the profile of the device assembly 100 either using a scope positioned within the stomach (not shown) or non-invasive imaging such as ultrasound or a radiographic imaging. Alternatively, or in combination, the active profile can be achieved after a pre-determined volume of fluid, liquid and/or gas is delivered to the reservoir 104. Furthermore, variations of the device can include one or more markers (such as radiopaque markers) 116 allowing a physician to determine orientation and/or size of the device assembly 100.

As noted above, this particular variation of the assembly 100 includes a conduit 114 that is coupled to the skin 102 through the fluid path 112 and extends into the reservoir 104. Alternatively, a conduit 114 can be directly coupled to the skin. When the device assembly 100 achieves the active state the conduit 114 can be pulled from the device assembly 100. For those variations that employ a sealable fluid path 112, withdrawal of the conduit 114 causes the sealable fluid path 112 to collapse or be compressed thereby preventing the contents of the reservoir 104 from escaping from the device assembly 100. Alternatively, or in combination, the sealable fluid path 112 located within the reservoir 104 can be sealed due to the increased pressure within the reservoir. In other words, the same pressure within the reservoir 104 that causes expansion of the device 100 also causes the sealable fluid path 112 to close, compress or otherwise reduce in diameter to a sufficient degree that material is unable to escape from the reservoir through the sealable fluid path 112.

In certain variations, the conduit 114 is held in place in the sealable fluid path 112 by friction alone. Withdrawal of conduit occurs by pulling on the conduit in a direction away from the device 100. During the initial stages of this withdrawal activity the expanded device 100 generally moves upwardly with the conduit in the stomach, until the expanded device 100 reaches the esophageal sphincter. With the device assembly restrained from further upward movement by the sphincter, the conduit 114 may then be withdrawn from the fluid path and from the patient by additional pulling force.

Upon withdrawal of conduit 114 the fluid path effectively seals, as described herein, and prevents migration of fluids or other substances into and out of the reservoir. In certain variations the fluid path seals on its own after removal of a conduit or other member located therein. In additional variations, hydrostatic pressure and/or pressure caused by the expanded filler acting along the length of the fluid path can aid in sealing of the fluid path.

FIG. 1F illustrates a state of the device assembly 100 (where this variation, unlike the variation of FIGS. 1D and 1E, includes a filler material 108 that swells within the device) after a physician or the patient desires to initiate release the device assembly 100 from the body. As discussed above, an exogenous material 120 is delivered into the stomach (or other portion of the body as applicable). As the exogenous material 120 (or exogenously activated body fluids) engage the release material 106, the release material reacts to the conditions created by the exogenous material and begins to degrade, melt, break down, or otherwise become unstable such that the physical barrier of the skin 102 becomes compromised. As noted above, additional variations of the devices can be used with an exogenous stimulus in place of or in addition to an exogenous material. For example, the exogenous substance can directly act upon the release material such as providing a substance at an elevated temperature and/or PH level that causes disruption of the release material to allow the filler material to interact with the fluids in the stomach and/or to pass from reservoir into the stomach. Alternatively, the exogenous material can interact with fluids within the body to directly or indirectly activate and/or degrade the release material.

In alternate variations, the release material, or additional areas on the skin degrade or become unstable due to the passage of time in the normal gastric environment. In such cases, the additional areas can serve as a safety mechanism to ensure release of the device after a pre-determined period of time. For example, in the variation shown in FIG. 1F, one of the areas of release material 106 can be responsive to exogenous stimulus or exogenous materials while the other release material 106 can break down over time. Alternatively, or in combination, as shown in FIG. 1F an exogenous stimuli can be used in combination with the exogenous material 120 to cause disruption of the release material. In another variation, the exogenous stimuli 130 can be used to act directly on the release material 106 (without any exogenous material) to cause disruption of the release material 106 and to begin the process of releasing the device assembly 100 from the patient.

FIG. 1F illustrates the filler material 108 escaping from the reservoir 104 as the device assembly 100 decreases from its active profile to allow for passage of the skin 102 and filler material 108 from the body. In certain variations, the consistency of the escaping filler material 108 is similar to or closely approximates the consistency of a food bolus. The matching of the consistency of the filler material to naturally occurring particles that travels within the body ease the passage of the filler material 108 through the remainder of the digestive tract. In certain situations, the instability or degradation of the release material 106 allows bodily fluids to mix with the content of the reservoir 104, which liquefies the filler material and expedites reduction of the device assembly 100 from an active profile or state. Although not illustrated, as the device assembly reduces in profile, the peristaltic movement of the muscles in the digestive tract works to extrude materials out of the device 100, allowing for the passage of the skin 102 of the device 100 through the digestive tract until it is ultimately excreted from the body. Certain variations of the device assembly can be made to have a soft, lubricious and/or malleable configuration to aid in passing through the gastrointestinal tract.

FIGS. 1A to 1F are intended to illustrate variations of devices and methods for occupying space within a patient's body, especially those devices for use within a gastric space. However, the principles described above can be used with any number of variations of the device as described below. As noted herein, combinations of different variations of devices, as well as the combinations of aspects of such variations are considered to be within the scope of this disclosure where such combinations do not contradict one another.

Figure 2:
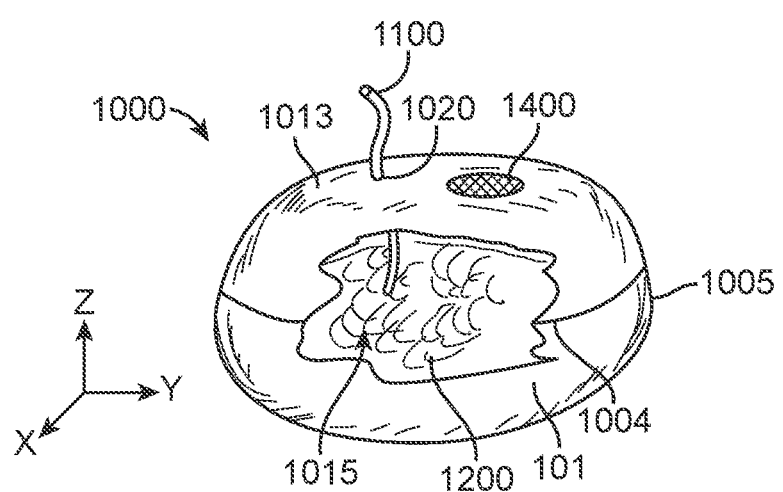
FIG. 2 shows a device assembly or construct in a hydrated or active profile whose outer "skin" defines a material reservoir or pocket.

In the embodiment shown in FIG. 2 the construct 1000 is in a hydrated or active profile and comprises a generally oblate spherical shaped structure whose outer "skin" defines a material reservoir or pocket 1010. The reservoir 1010 is bounded by a thin, flexible material surface or skin 1013 that encloses an interior volume 1015 for retaining substances that maintain the construct in the active profile. In one such variation, the reservoir 1010 contains a filler material 1200, which may be a liquid or a semi-solid or gel-like material. In general, the volume of filler material 1200 is initially low, that is, when construct 1000 is in its initial, pre-deployment condition. The volume of filler material 1200 increases after the construct's deployment. Construct 1000 in FIG. 2 illustrates the fully expanded or active state but for clarity only a representative portion of filler material 1200 is shown.

The transition from initial, unexpanded state construct 1000 to the active state can be effected by increasing the volume of filler material 1200 enclosed in reservoir 1010. Additionally, the volume can be expanded through expansion and/or swelling of the filler material already inside the reservoir 1010. For example, as was described in commonly assigned U.S. patent application publication number US2011/0295299, one exemplary embodiment filler material 1200 in the initial state is a pre-determined volume of dry hydrogel granules. The dry hydrogel granules can swell, for example, between 10 and 400 times their dry volume when exposed to an appropriate liquid, generally an aqueous solution.

In the variation shown in FIG. 2, once a medical practitioner or user deploys of the construct 1000 into the stomach, the aqueous liquid in the stomach migrates into the reservoir 1010 and creates a slurry of liquid and substantially fully hydrated hydrogel. As is well known, hydrogels absorb water from their surroundings causing swelling of the hydrogel. In the embodiment of FIG. 2, the volume of dry hydrogel is pre-selected to have a fully swollen, unconstrained volume that slightly exceeds the volume of the reservoir 1010. Under constraint, hydrogels cannot swell to a greater volume than the limits of the constraining volume; however, constrained hydrogels can and do exert pressure against the constraint. Thus, reservoir 1010 becomes a structurally self-supporting structure, when filled with an excess of swollen hydrogel (that is, when the unconstrained volume of the swollen hydrogel is greater than enclosed interior volume 1015). In other embodiments, reservoir 1010 is filled and pressurized with other filler. In its expanded state, reservoir 1010 can be sufficiently elastic to deform under external pressure and returns to its pre-deformation shape when the pressure is removed. In yet additional variations, the filler material can be selected such that it hardens after a period of time to become its own skeletal structure or to support the skin. Such a filler can be selected to eventually degrade based on the environment in the stomach or digestive tract.

Assemblies 1000 under the present disclosure can comprise a material surface or skin 1013 that is substantially impermeable to liquids and/or gases. In these embodiments, filler material 1200 can be, respectively, a liquid or a gas. Additionally, filler material 1200 can be a fluid-swellable material such as hydrogel, which, when hydrated, becomes a solid, semisolid or fluid-like gel or slurry. As illustrated in FIG. 2, embodiments comprising a substantially impermeable skin 1010 further comprise a fluid transport member 1100 that allows for the migration of fluid through the skin. In some examples, as noted above, the fluid transport member includes a sealable fluid path that may or may not be coupled to an additional fluid conduit. In additional variations, the fluid transport member can include a localized liquid transfer member 1100 that is disposed in an orifice 1020 through the skin 1013 and facilitates the migration of fluid between the interior and exterior of reservoir 1010. One such example can be found in U.S. Provisional application entitled "Resorbable Degradation System" Ser. No. 61/723,794 filed on Nov. 8, 2012, the entirety of which is incorporated by reference herein As noted above, in certain variations, where the device assembly 1000 comprises a substantially liquid impermeable material surface, a construct 1000 in the expanded active profile can remain in stomach or other portion of the body indefinitely until released. Therefore, as noted above, devices of the present disclosure can include a release material 1400, which allow the construct 1000 to reduce in size from the active profile and ultimately pass through the body. Such an active release material 1400 configuration allows for on-demand release of the construct. As noted above, once activated, degraded, or otherwise made unstable, the release material allows migration of filler material from the reservoir and device assembly. In some variations, activation of the release material opens a passage in the skin 1013 of the device 1000. Alternatively, or in combination, activation of the release material can result in reduction of the integrity of the skin forming the barrier about the reservoir. Once the barrier is compromised, the filler material can safely pass into the body. Regardless of the means, the activation of the release material and release of the filler material collapses the device 1000 leading to egress or removal of the device 1000 through the body (in this variation through the lower gastro-intestinal track). As noted above, variations of the devices described herein include a release material that is activated by exposure to an exogenous substance.

In certain variations, the device assembly 1000, in the active profile, comprises a highly oblate spheroid wherein the skin 1013 can be a thin, film-like material that is soft, tear-resistant, flexible, substantially inelastic, and non-self-adhesive. Such features can be beneficial for a device that is to be compressed into a small oral dosage form for administration. In certain examples, the skin 1013 comprised a 0.0015 inch thick polyether polyurethane film. In a simple variation, an oblate spheroid can be created from skins forming an upper material surface and a lower material surface, wherein upper material surface and lower material surface are sealed to each other as shown by seam 1004 in FIG. 2. One such means for sealing the device 1000 comprises an ultrasonic or radio-frequency (RF) weld around the periphery of the surface materials. As will be described in more detail below, in a possible assembly method, the upper and lower material surfaces are formed as nominally identical, substantially disk-like shapes of material, welded in a band around most of their circumferences, the assembly is then inverted (turned inside out) through an unwelded section. Once the assembly is inverted, the welded material forms the seam 1004 that projects inwardly.

In some variations, as illustrated in FIG. 1C, the release material can comprise a filament, clip, band, cap, or other structure that mechanically closes the edges of the skin. Further, as described below, a source of stored energy, such as a loaded spring or compressed sponge or other material, may be included in the release assembly, where such kinetic energy is also released upon activation of the release material and which may improve the performance of such assembly.

Figure 3:
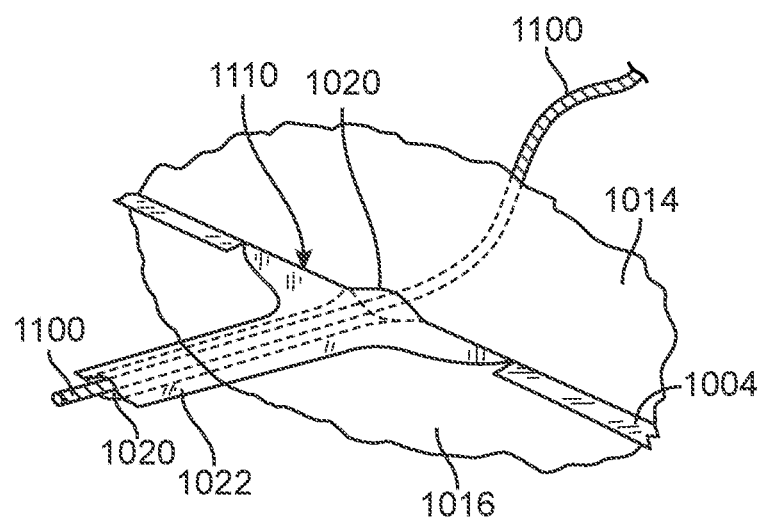
FIG. 3 illustrates a variation of a fluid transfer member also having a sealable fluid path for use with the device assemblies described herein.
Figure 4:
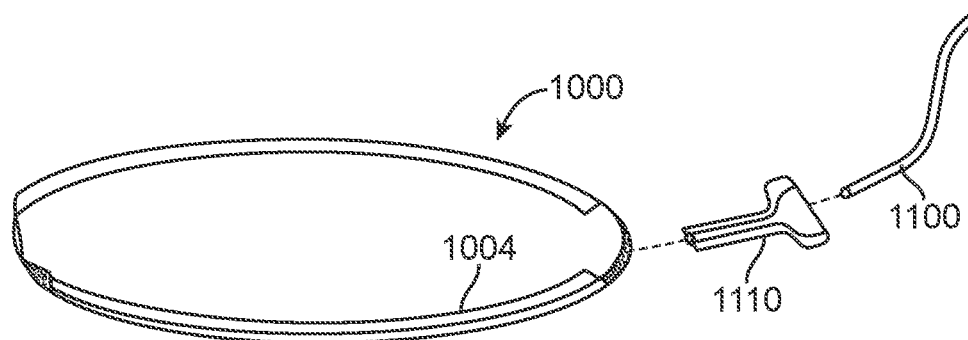
FIG. 4 shows a schematic perspective view of a variation of a tunnel member being installed during fabrication of the device assembly.

FIG. 3 illustrates a variation of a fluid transfer member 1100 also having a sealable fluid path 1110 for use with the device assemblies described herein. In this example the fluid transfer member 1100 also includes an elongate fluid conduit, or tube, that passes through a tunnel member that functions as a sealable fluid path 1110. The tunnel member 1110 can be positioned in an orifice in the upper 1014 or lower 1016 material surfaces or, as illustrated in FIG. 4, in an opening in a seam 1004 of the device assembly. This variation of the tunnel member 1110 comprises an elongate portion 1022 that extends within the reservoir of the device assembly. In some variations, the tunnel member can extend beyond the seam 1004 or beyond the exterior surface of the device assembly as discussed above.

As illustrated in FIG. 3, a portion of the fluid transport member includes a tunnel member 1110 that can comprise two layers sealed along their edges, forming an extended orifice 1020 or lumen. In additional variations, the tunnel member 1110 can comprise a tube structure having a single continuous wall that defines a passage therethrough. In yet additional variations, a tunnel member can include more than two walls. Regardless of the configuration, the wall or walls of the tunnel member are predisposed to occluding or blocking flow through the tunnel member by obstructing the orifice or passage 1020.

The orifice or lumen 1020 forms a fluid path that allows a remainder of the fluid transport member 1100 to deliver fluids into the reservoir. In this variation the fluid transport member 1100 further comprises a conduit. However, as noted herein, the fluid transport member can comprise a wick type device or any fluid source that allows delivery of fluids into the reservoir of the device. As also noted herein, a variation of the device comprises an attachment of conduit 1100 to a portion of tunnel member 1110, wherein the attachment may be direct or indirect and wherein, in some variations the attachment is releasable to permit conduit 1100 to be detached, withdrawn, or removed from the tunnel member 1110. Withdrawal or removal of conduit 1110 from orifice 1020 permits the tunnel member 1110 to prevent egress of fluids or other substances from within the reservoir. Sealing of the tunnel member 1110 can occur via a rise in pressure within the reservoir. Alternatively, or in combination, a number of other mechanisms can result in sealing or closure of the orifice 1020 in the tunnel member 1110. For example, in additional variations the surfaces forming the lumen 1020 can seal upon contact or the length of the tunnel member 1110 combined with its flexible nature can simply make it difficult for substances, such as an expanded hydrogel, to travel through the elongated portion 1022 of the tunnel member.

FIG. 3 also shows the conduit 1100 extending through the tunnel member 1110 such that it extends into the reservoir. However, in alternate variations, the device end of conduit 1100 can remain within an interior of the orifice 1020 of the tunnel member 1110. In such a variation a distal end of the distal portion of the fluid conduit remains within the elongated passage of the fluid tunnel and can rely on flow pressure to propel the liquid through a portion of the tunnel member such that the fluid ultimately ends up in the reservoir.

In one variation of the tunnel member 1110, as illustrated in FIG. 4, the tunnel member 1110 shaped roughly as the capital letter T, wherein the vertical stem of the T comprises the elongate passage 1022 and wherein the crossbar of the T, in part, forms an increased attachment surface that can be attached to the skin as noted above. As may be seen in FIG. 4, tunnel member 1110 can be disposed through an opening in the seam 1004. In other variations tunnel member 1110 can be formed as part of the upper 1014 or lower 1016 material surfaces. That is, the templates that are used to cut the upper and lower material surface layers can include elongated tabs that correspond to the upper and lower layers of elongate passage 1022. The seams of said tabs may be sealed during the process of sealing the upper and lower material surface layers, leaving an unsealed, axially extended orifice in the center of the elongate tabs.

Some examples of materials used to form a tunnel member include thin, film-like materials. For example, variations include tunnel member materials that have properties similar to the material used in material surface or skin of the device. Additional materials include but are not limited to polyurethane, nylon-12, and polyethylene. In certain variations, Suitable materials typically have a durometer hardness of 80 Shore A or softer and are extruded with a glossy finish to enhance cohesion and tackiness. Layers of material in exemplary tunnel members can typically be between 0.001 inch or less and 0.1 inch thick. In one example a tunnel member includes a single layer thickness of 001 inch. One suitable layer material, which is a 0.001" thick, high tack urethane film, is available as part number MT1001 NL from American Polyfilms.Inc, 7 Business Park Dr., Branford, Conn. 06405.

The length of the elongate portion 1022 that extends within the reservoir of the device assembly may be short, for example, 0.1 inch or as long as the diametric width of the device assembly. In one exemplary valve the length within the reservoir is approximately 1.25 inches and the width of that portion is approximately 0.75 inches wide.

Figure 5:
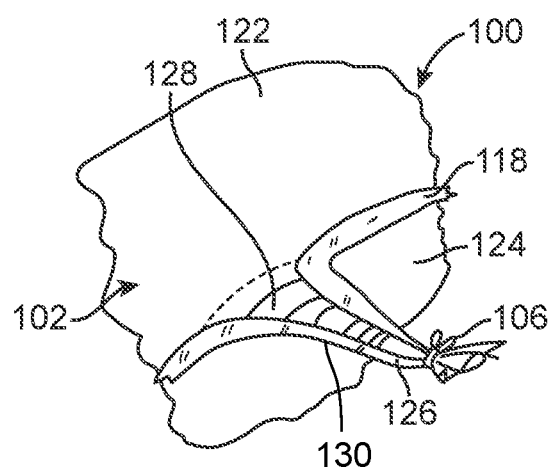
FIG. 5 illustrates a partial view of a variation of an inverted section of a skin of a device assembly closed by a release material.

As discussed above, variations of a device assembly include a release material that is coupled to a portion of the skin to form a barrier to retain substances within a reservoir of the device. FIG. 5 illustrates a partial view of a variation of an invaginated section 126 of a skin 102 of a device assembly 100. As discussed herein, the skin 102 can include a first surface 122 and second surface 124 joined at a seam 118. The seam 118 can include any number of unjoined sections that are intended to function as release areas 128. In the illustrated example, the release area 128 is bounded by an inwardly directed, or inverted section 126, of the skin 102. The particular illustrated embodiment of inverted section 126 is also known as the invaginated section 126, so named as it may comprise a tuck, fold, pucker, bulge, extension, etc. in the skin 102. Alternatively or in addition, the inverted section 126 can be formed within a first 122 or second 124 surface of the skin 102 rather than within a seam 118

The release area 128 of the invaginated section 126 ordinarily forms a passage that is fluidly sealed by a release material 106. The release material can comprise a mechanical closure (such as a staple-type structure or a filament that ties together the invaginated structure). Alternatively, or in combination, the release material 106 can comprise a temporary seal or other joining of the edges of the invaginated section 126. In additional variations, the release material can extend outwardly from an exterior surface of the skin. In some variations, the release material 106 is disposed on the invaginated portion 126 sufficiently close to the skin to be affected by a temperature increase caused by delivery of the exogenous substance.

In certain variations, the inverted section 126 forms a release area 128 that provides a passage to provide fluid communication between the reservoir and the exterior of the device assembly. This feature allows release of any fluids or material retained within the reservoir to allow the device to reduce in size and pass from the body. The opening can be located at the end of the passage, i.e., at the open edge of the material that is closed together. Alternatively, the wall forming the passage can be porous in an area beyond the point at which the inverted section 126 is bound (e.g., the area disposed inwardly relative to release material 106).

In additional variations, the inverted section 126 includes an energy storage element that encourages a rapid and more complete opening of the release area 128. Variations of the internal energy storage element can include a solid structure, or a structure that allows passage of fluids. The energy storage element can include a compressible elastic material, for example, a latex foam. In some variations internal energy storage element is generally cylindrical with a diameter at least fractionally smaller than the diameter of the passage in the inverted section 126. When device 100 is deployed in the body, release material 106 is tied firmly around the inverted section 126 at the position of the internal energy storage element, thereby simultaneously sealing the invagination and compressing the internal energy storage element. The resilience of the elastic material in the internal energy storage element creates a tensile force in release material 106 that is greater than the tension in the release material tie used to seal an invagination alone.

Figure 6:
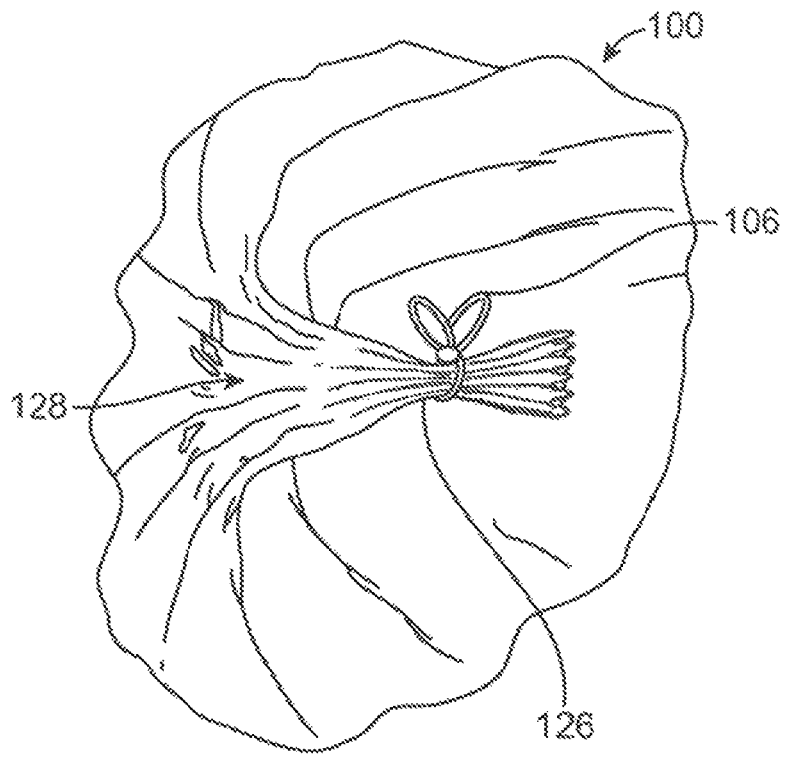
FIG. 6 illustrates a cutaway view of the interior of a device assembly comprising an inverted section of the skin further that opens the device to release the contents of the device.

FIG. 6 illustrates an example of an inverted section 126 that is pleated or folded and restrained by a release material 106. The optional energy storage element, if used, is not shown in FIG. 6 for sake of clarity. However, variations of the devices can include energy storage elements that are located between folds or folded into the inverted section 126.

In another variation, not illustrated, the energy storage element is disposed outside of inverted section 126. An external energy storage element, for example a retaining ring, is used to increase the tension in the cinched and tied filamentary release material 106. The increased tension encourages the release material to break apart sooner, more rapidly, and more completely than it otherwise would. A suitable external energy storage element may be made using, for example, a special order, 5 millimeter diameter, Hoopster® retaining ring, available from Smalley Steel Ring Company, 555 Oakwood Road, Lake Zurich, Ill. 60047.

The release area 128 in each of the variations of the inverted section 126 is initially sealed or closed off by a release material that is coupled, directly or indirectly, to a portion of the skin to form a barrier to retain substances within a reservoir of the device. In many variations the release material is filamentary. Examples of release materials that are available in filamentary form can include Polyglycolide (PGA), Polydioxanone (PDS), Poly(lactic-co-glycolic acid) (PLGA), Polylactide (PLA), Poly (4-hydroxy-butyric acid) (P4HB), Polyglactin 910, and Polycaprolactone (PCL).

In such variations, the release material in the expanded device assembly degrades over time by hydrolysis where the rate of hydrolysis varies with material selection and liquid filler pH. In variations wherein the release material is PCL the release material can also degrade by elevating the temperature of the release material since PCL softens, melts, and weakens above a pre-determined temperature. In some cases the pre-determined temperature is greater than normal body temperature. Accordingly, in such variations, the exogenous substance can comprise a heated fluid that can raise the temperature of the PCL without causing injury to the adjacent areas of the body. As the PCL release material degrades, the structural integrity of the joined region of the release section (such as the inverted section 126) decreases.

In one example, the release material is a modified PCL, wherein the modification comprises lowering the melting point of unmodified PCL from its normal melting temperature to a human-tolerable temperature.

Examples of the release material can include poly(caprolactone) or PCL. In such variations, PCL softens, melts, and weakens above a pre-determined temperature. In some cases the pre-determined temperature is greater than normal body temperature. Accordingly, in such variations, the exogenous substance can comprise a heated fluid that can raise the temperature of the PCL without causing injury to the adjacent areas of the body. As the PCL release material degrades, the structural integrity of the joined region of the release section (such as the invaginated section 126) decreases. In one example, the release material is a modified PCL, wherein the modification comprises lowering the melting point of unmodified PCL from its normal melting temperature to a human-tolerable temperature.

For example, an on-demand degrading construct composed of nylon-12 can be constructed by first fabricating a 1" circular annulus of 1.5 mil Pollethane, also known as 55DE Lubrizol 2363 polyether polyurethane (available from Specialty Extrusions Inc. of Royersford, Pa., USA). A circular degradable patch of poly(caprolactone) (PCL) (with a modified melting point, $T_m$, equal to ~47° C.; available from Zeus Industrial Products of Charleston, S.C., USA) can be RF-welded to the Pellethane annulus, covering the hole, creating a $T_m$-modified PCL patch surrounded by a rim of Pollethane. The Pollethane rim can then be RF-welded to a sheet of nylon-12, which can then be used for further construction.

Examples of release materials can include biocompatible manufactured polymers. Table 1 is a compilation of the degradation properties of several biocompatible materials that can be extruded or otherwise manufactured in filamentary form and which also can be predictably degraded. Some of these materials, poly(vinyl alcohol) are stable in dry environments but dissolve very quickly in moist environments. Some biocompatible polymers, for example co-polymers of methacrylic acid and methyl-methacrylate, dissolve in liquids having physiologically relevant pHs. For example, they remain stable at pH<7.0 but dissolve at pH>7.0. Other polymers, for example Poly(caprolactone), remain stable at typical gastric temperatures but melt in seconds at temperatures above a pre-determined melting point.

In some variations, polymers that degrade by gradual hydrolysis may be used for the release material. The degradation times of various polymers, under various degradation conditions, can range from about 2 weeks to about 6 months, where the degradation time depends on parameters such as degradation liquid pH, suture construction (e.g., stranded or monofilament), and filament diameter. In general, polymers last longest when exposed to distilled, neutral pH water and degrade more quickly when immersed in acidic or basic pH liquid.

The degradation times for several exemplary materials are tabulated in Table 1. The experimentally determined degradation times in the table were determined in simulated use conditions; that is, as illustrated in FIG. 6, the release material 106 was coupled to an example or simulation of an inverted section 126 that is pleated or folded.

TABLE 1

Exemplary Release Material Properties

| Polymer | Degradation Mode | Degradation Condition | Degradation Time |
|---|---|---|---|
| Poly(glycolic acid) | Gradual hydrolysis | Exposure to water or acid | ~2 weeks |
| Poly(dioxanone) | Gradual hydrolysis | Exposure to water or acid | ~1 to 2 months |
| 1 PDO | | 0.9% benzyl alcohol | 54 days |
| 3-0 PDO | | distilled water | 56 days |
| 4-0 PDO | | distilled water | 60 days |
| 4-0 PDO | | 0.9% benzyl alcohol | 62 days |
| 3-0 PDO | | 0.9% benzyl alcohol | 65 days |
| Poly(lactic-co-glycolic acid) | Gradual hydrolysis | Exposure to water or acid | ~1 month |
| 3-0 PLGA | | distilled water | 25 days |
| Poly(vinyl alcohol) | Rapid dissolution | Exposure to any aqueous solution | Seconds |
| 4-0 Monocryl | | distilled water | 27 days |
| 2-0 Vicryl | | 0.9% benzyl alcohol | 43 days |
| 2-0 Vicryl | | distilled water | 43 days |
| 0 Vicryl | | distilled water | 46 days |
| 0 Vicryl | | 0.9% benzyl alcohol | 48 days |
| 1 Vicryl | | 0.9% benzyl alcohol | 53 days |
| 1 Vicryl | | distilled water | 53 days |
| Methyacrylic acid methyl-methacrylate co-polymers | Hydrolysis; on-demand pH-dependent dissolution | Exposure to alkaline pH | Days at near neutral pH and minutes to hours at alkaline pH |
| Poly(caprolactone) | Hydrolysis; on-demand at temperatures greater than 60° C. | Exposure to heat | 6 months at temperatures less than melting point, seconds at or above melting point |

As the release section opens the reservoir to the surrounding environment the opening provides an open path out of the device assembly. The open path allows the contents of the device assembly, such as the filler material, to become exposed to the gastric contents and freely to exit reservoir. When positioned within the stomach, normal gastric churning assists in emptying the contents of the device assembly allowing for the entire device along with its contents to pass from the body. In some variations, the membrane that forms the skin will provide little or no structural support. This configuration allows the body's natural squeezing strength to be sufficient to extrude any reasonably viscous substance out of the device assembly.

Figure 7:
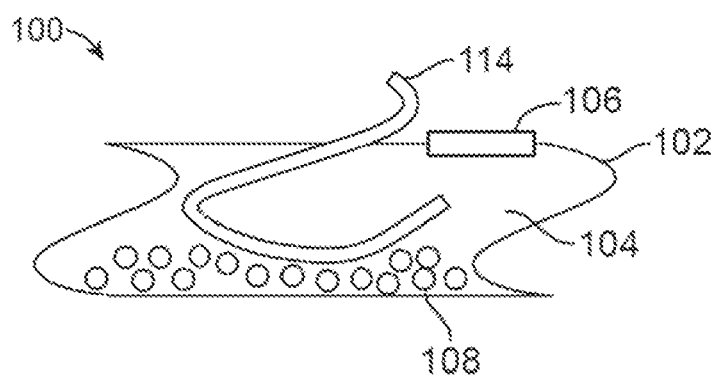
FIG. 7 provides a schematic illustration of another example of a device assembly having a release material located on a surface of the skin.

FIG. 7 provides a schematic illustration of another example of a device assembly 100 having a release material 106 located on a surface of the skin 102. One example of such a release material comprises a degradable patch 106 that, when degraded, opens the physical barrier surrounding the reservoir 104 to allow filler material 108 (swollen or unswollen) to exit the device assembly 100. The device assembly 100 comprises a skin material to which release material 106 can be joined (e.g. by heat sealing, RF-welding, impulse heating, or any other means). In certain variations, the release material/degradable patch 106 comprises a material or combination of materials that remains impermeable to water and hydrogel after deployment and can be degraded "on-demand" in response to an exogenous substance or in response to a condition created within the body being the result of the administration of the exogenous substance.

In one example, the release material can range from 25 microns thick; up to 2.5 millimeters thick. In another example, release material is a modified poly(caprolactone) with melting point $T_M$=47° C. (available from Zeus Industrial Products of Orangeburg, S.C. USA). In additional embodiments, degradable patch 106 may be poly(glycolic acid) or poly(L-lactide acid) (available from Poly-Med, Inc of Anderson, S.C.).

Material Surface or Skin

The type of material or skin will depend upon the intended application. In some variations, a skin will be chosen as a balance of selecting a sufficiently thick film-like material that has adequate strength. For example in some variations, tear resistance can be preferred to enable the finished construct to be compression into as low a volume capsule as possible. The inventors have determined that thin films with a thickness ranging from 0.5 mils to 4 mils are generally suitable. However, the devices described herein can comprise a greater range of thicknesses depending upon the particular application, including a range of thicknesses in different parts of the same construct. In some embodiments, the film-like material must be weldable or adherable to other materials such as might be used in valves 1110, filler material release mechanisms 1400, and/or attachment interfaces as described herein.

In additional embodiments, the film-like material exhibits low transmission rate of filler material, both before and after device expansion. In some embodiment the film-like material exhibits a low moisture vapor transmission rate. Additionally, some film-like material also exhibits high chemical resistance to the variable conditions encountered in the stomach. These conditions include low pH, high salt, high detergent concentrations (often in the form of bile salt reflux), enzymatic activities (such as pepsin), and the variable chemistries of chyme that depend upon the nature and content of consumed food. For those devices used in the gastric space, the material must also be comprised of biocompatible materials that can safely be in contact with the gastric mucosa for the duration of the treatment course.

The devices described herein can use numerous thermoplastic elastomers, thermoplastic olefins and thermoplastic urethanes that can be extruded or cast into single-layer or multi-layer films which are suitable for embodiments of the gastric device. Example base resins that may be employed include polypropylene, high-density polyethylene, low density polyethylene, linear low density polyethylene, polyester, polyamide, polyether polyurethane, polyester polyurethane, polycarbonate polyurethane, bi-axially oriented polypropylene, Polyvinylidene chloride, ethylene vinyl alcohol copolymer, and Ethyl Vinyl acetate. Some embodiments comprise single layer films whilst other embodiments comprise multiple layer films. Other embodiments consist of multilayer films including one or more tie layers to prevent layer separation.

In some embodiments, the film-like material may be coated with other materials. For example, in some embodiments hyaluronic acid coatings can be employed to improve softness and lubriciousness. In other embodiments, coatings such as Parylene® can be applied to improve the chemical resistance of the gastric mucosa-exposed film surface. In some embodiments, wax coatings, PVDC coatings, vacuum-metallization, or Parylene® coatings may be applied to the surface of the film to reduce its moisture vapor transmission rate.

In one example, the film-like material used comprised a 1.5 mil polyether polyurethane film. In other embodiments the film-like material is a 1 mil nylon 12 film or a 1.5 mil LLDPE film. In another example, the film-like material consisted of a multi-layered structure comprising an outer layer of polyurethane, a middle layer of PVDC or EVOH, and an inner layer of polyurethane.

Filler Material

The devices described herein can be filled to temporarily occupy a space within a patient in any different number of ways. In one variation, the devices can use a fluid filler material that is delivered to the device upon positioning within the body. In another example, the devices can be filled with a swellable material that is in an unswollen state during ingestion and swells when hydrated by gastric liquids or an exogenous liquid. Generally, a swellable filler material that has a high swelling capacity and achieves a semi-solid consistency is useful to enable the finished construct to be compressed into as low a volume initial state as possible but still maintain rigidity once expanded. However, unless specifically noted, variations of the device can employ a number of different types or combinations of filler materials. During various experiments, it was determined that superabsorbent hydrogel polymers with a mass:mass swelling capacity of between 100 and 1000 are generally suitable, where a mass:mass swelling capacity of 100 is defined herein to mean that 1.0 g of dry hydrogel will absorb water and swell to become a semi-solid mass of 100.0 g.

Typically, suitable hydrogels swell maximally in the presence of distilled water and a number of these hydrogels also de-swell (releases bound water) in the presence of the variable environmental parameters encountered in the stomach. For instance, parameters such as pH, salt concentration, concentrations of emulsifying agents (often in the form of bile salt reflux), enzymatic activities (such as pepsin), and the variable chime chemistries, which depend upon the nature and content of consumed food can affect the swelling/deswelling behavior of certain hydrogels. Typical hydrogel swelling times range from between 5 minutes and 1 hour. In one variation, the hydrogel fully swells in under 15 minutes and fully de-swells in less than 10 minutes after exposure in certain environments. Many hydrogels are supplied with particle sizes distributed between 1 and 850 microns. In certain variations, gastric applications benefit from the use of hydrogel particle sizes distributed between 1 and 100 microns. In addition, the hydrogel must also be comprised of biocompatible materials that can be safely in contact with and excreted by the gastrointestinal tract. Examples of such biocompatible superabsorbent hydrogel polymers that possess swelling capacities, swelling times, and de-swelling times suitable for embodiments of gastric construct include poly(acrylic acid), poly(acrylamide), or co-polymers of poly(acrylic acid) and poly(acrylamide). Another such material that can be used as a filler material is a crosslinked poly(acrylic acid) with particle size distribution ranging from 1-850 microns and swelling capacity of 400.

Shapes

As discussed above, certain variations of the device approximate a highly-oblate spheroid comprising a diameter in the X-Y plane and a thickness along the Z-axis as illustrated in FIG. 2. In certain variations, the expanded dimensions of the device assembly can range from having a diameter between 2 inches and 10 inches. In another embodiment, the diameter of the construct is approximately 4.6 inches. The Z-axis thickness can range between 2 inches and 5 inches. However, the device assembly, unless otherwise claimed, is not limited to any particular dimension. The data below of construct parameters provides the experimentally determined dimensions of two constructs having the oblate spheroidal shape.

| Parameter | Construct 1 | Construct 2 |
|---|---|---|
| Unexpanded diameter (inches) | 4.7 | 5.8' |
| Maximum swollen volume | 300 ml | 500 ml |
| Expanded diameter (inches) | 3.64 | 4.63 |
| Expanded thickness (inches) | 2.40 | 2.46 |

Liquid Transfer Valves

Figure 8:
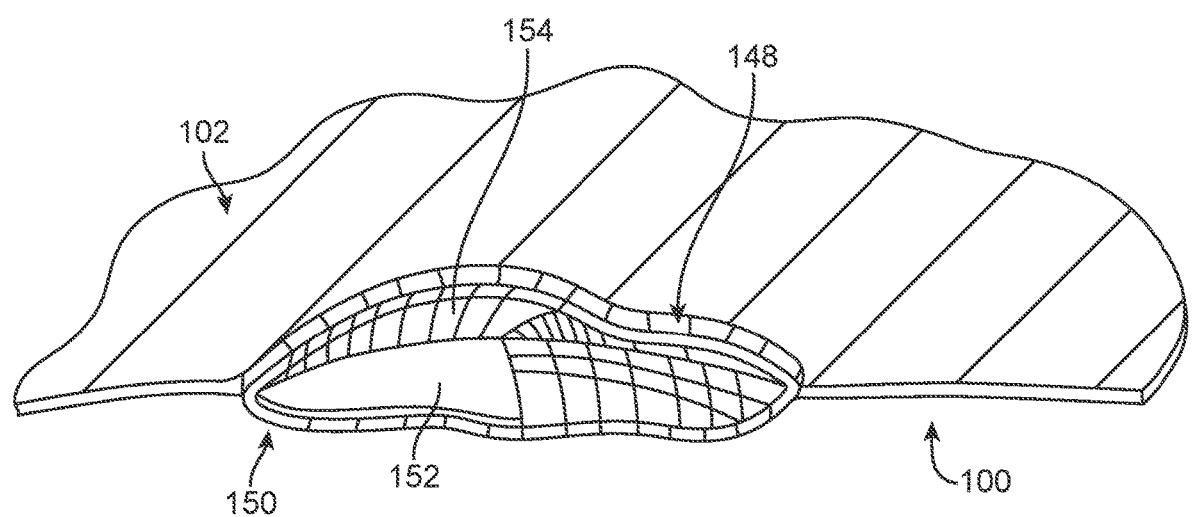
FIG. 8 shows an additional variation of a portion of a device assembly that provides a control over the fluid permeable path through otherwise impermeable material surface.

FIG. 8 shows an additional variation of a portion of a device assembly, in other embodiments liquid transfer member comprises a valve 150, wherein valve 150 is disposed in orifice 148 and provides a control over the fluid permeable path through otherwise impermeable material surface 102. In some embodiments valve 150 comprises a multilayer material structure composed of regions of permeability 152 juxtaposed against regions of impermeability 154, whereby fluid may transmigrate between the exterior and the interior of reservoir when the regions of permeability 152 and impermeability 154 are not pressed together in tight juxtaposition and whereby fluid is inhibited from transmigrating when the regions 152, 154 are pressed together tightly. In some embodiments valve 150 is self-closing. That is, valve 150 changes from allowing fluid transmigration to inhibiting fluid transmigration without external activation. In one embodiment valve 150 self-closes in response to the increasing pressure of the expanding filler material or increasing pressure within the reservoir, for example, swelling hydrogel pressing the regions 152, 154 sufficiently close together to form a barrier.

As noted above, the device assemblies described herein can include a fluid transport member 110 that serves to deliver fluids into the reservoir. One example of such a fluid transport member is a wick that includes a filamentary material capable of conducting a liquid from one end to the other by capillary action. The wick can extend from the interior of the device reservoir to outside the device skin, typically just several millimeters beyond the skin although longer wicks may be used. In another example, the liquid transfer mechanism 1100 comprises a fluid conduit 114, tube, or catheter that, after the device is extends from the deployed device in the patient's stomach to outside of the patient where it is connected to a source of filling fluid. In many embodiments the fluid flow through the fluid transport member is preferably shut off once the device has reached its desired deployment profile. In embodiments comprising a wick-like fluid transport mechanism the fluid flow may be shut off by pinching down on the wick while in embodiments comprising a catheter-like fluid transport mechanism the fluid flow is halted externally and the catheter-like mechanism is withdrawn from the device first and from the patient second. When the catheter-like mechanism is withdrawn from the device it is necessary to seal the orifice through which the catheter passed through the skin of the device. In many of the assemblies described herein fluid flow is inhibited by a self-sealing, two-layer valve. In other embodiments the self-sealing valve has more than two layers.

In yet other embodiments liquid transfer mechanism 1100 comprises a mechanical valve. Mechanical valves of suitably small dimensions, comprising biocompatible materials, are well known in the art and are commercially available. A mechanical valve that serves as liquid transfer mechanism 1100 comprises a one-way or "check" valve design which allows fluid to enter reservoir 1010 but prevents fluid from exiting the reservoir. Alternatively, a mechanical valve that serves as liquid transfer mechanism 1100 may have a normally open state but which self-closes when internal fluid pressure is greater than external fluid pressure.

Figure 9A:
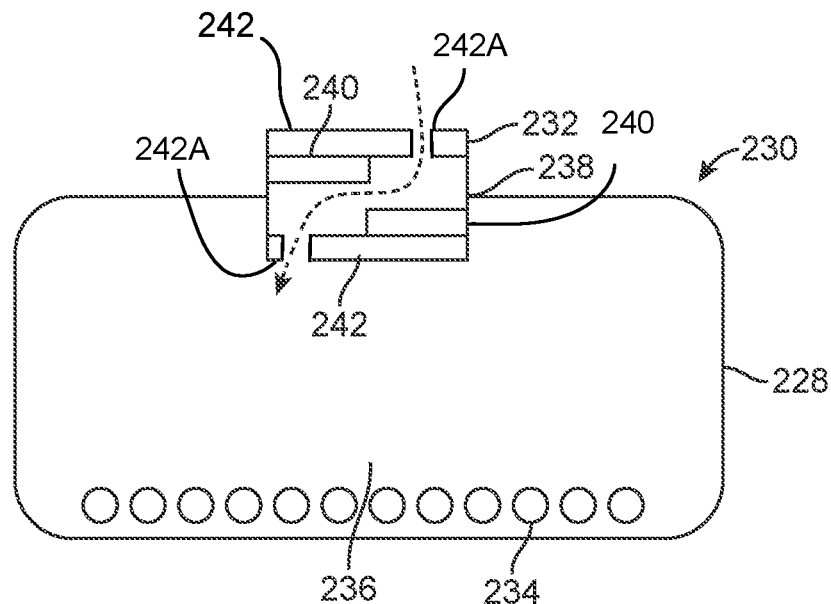
FIGS. 9A and 9B an example of a valve driven by expansion of filler material within a reservoir of the device assembly.
Figure 9B:
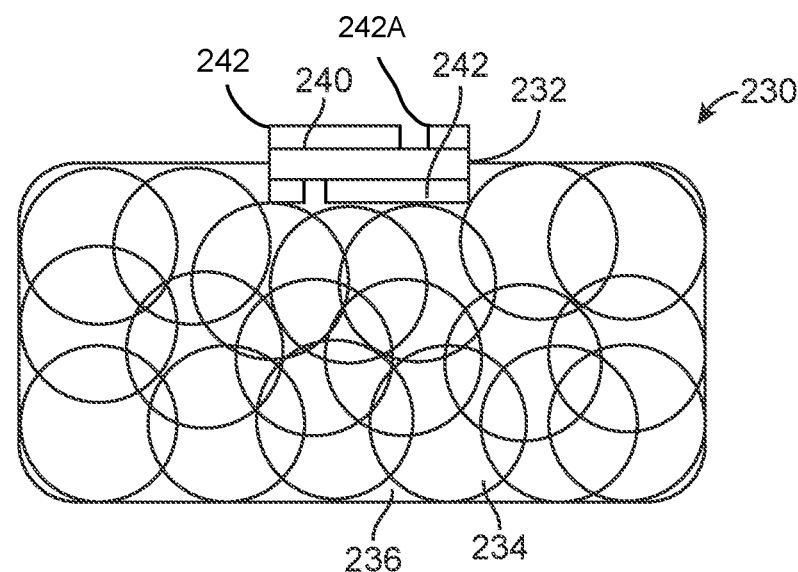

FIGS. 9A and 9B schematically illustrate one example of a valve that self-seals by the expansion of filler material 234 within a reservoir 236 of the device assembly 230. The valve 232 is positioned or otherwise disposed in an orifice 238 in the material surface or skin 228. In other embodiments orifice 238 may be an unsealed section of seam 1004, as illustrated in FIGS. 3 and 4. In the illustrated variation valve 232 comprises two material containment layers 242. Containment layers 242 are at least partially permeable to fluids but may be impermeable to non-fluid filler materials. This permeability may be achieved by a sieve-like structure or, as illustrated in FIG. 9A, permeability may be achieved by puncturing an impermeable layer with at least one hole 242. Valve 232 further comprises regions of flow control material 240. Flow control material 240 is substantially impervious to fluids, specifically to the fluid used as filler material 234 or to hydrate a dry mass of filler material. As illustrated, the regions of flow control material are disposed directly juxtaposed to the permeable regions of containment layers 242. During deployment there is initially no pressure within the device assembly. With no pressure the juxtaposed flow control material and fluid permeable regions of the containment layer are able to separate, creating a fluid flow path. This flow path is indicated by the dashed arrow in FIG. 9A. In some variations a fluid transfer member, not illustrated, is used to transfer fluid from outside the device assembly to the internal reservoir. In these variations the containment layers may be made from fluid impermeable material with a hole in each containment layer to allow the selected fluid transfer member to pass into the reservoir. The transfer member is inserted through the valve prior to deployment. In some variations the transfer member is a wick while in other variations the transfer member is a fluid conduit or catheter.

FIG. 9A also illustrates a pre-determined amount of filler material 234 within the reservoir 236. In some variations, the pre-determined amount is generally measured by dry mass. The dry mass of filler material 234 is determined by the amount of filler material 234 needed to fill the known volume of the expanded device 230 when the filler material is fully hydrated. When expanded, the filler material applies a pressure within the reservoir 236, which provides a shape-restoring force that resists externally applied deforming forces. In other variations filler material 234 is not pre-loaded within reservoir 236. In these variations the filler material is a fluid or slurry material delivered through a fluid transfer member, generally embodied as conduit 114, as shown, for example, in FIG. 1D.

FIG. 9A also shows valve 232 filling orifice 238. This variation of the valve 232 includes one or more flow control layers 240 that aid in closing of the valve upon action by the filler material 234. FIG. 9B illustrates expansion of the filler material 234, which increases pressure against the valve 232 and closes the fluid path by pressing the flow control layers 240 toward their respective material containment layers such that the fluid path is closed.

In some variations the design may be simplified to comprise just two layers of fluid impermeable material through which passage holes have been created to allow the fluid transport member to pass. This variation is discussed further below in conjunction with FIGS. 9C and 9D.

Turning back to FIG. FIG. 9A, before filler material 234 expands, valve 232 is fully open; that is, it allows fluid to pass through the valve in either an inward or outward direction. On the other hand, after filler material 234 expands, typically via hydration, the valve 232 fully closes, as shown in FIG. 9B.

In some embodiments valve 232 comprises a filler material containment layer 242. Generally, containment layer 242 is at least partly fluid permeable and simultaneously able to contain filler material 234, in its dry or its hydrated state, within device 230. In some embodiments filler material containment layer 242 is also a flow control layer; that is, a single layer in valve 232 can simultaneously be a part of the flow control function of valve 232 and perform the filler containment function of containment layer 240. For example, laser micromachining may be used to create microperforations in one region of an otherwise fluid impermeable membrane. The microperforated region functions as the containment layer while the unperforated region can function as the flow control layer.

Figure 9C:
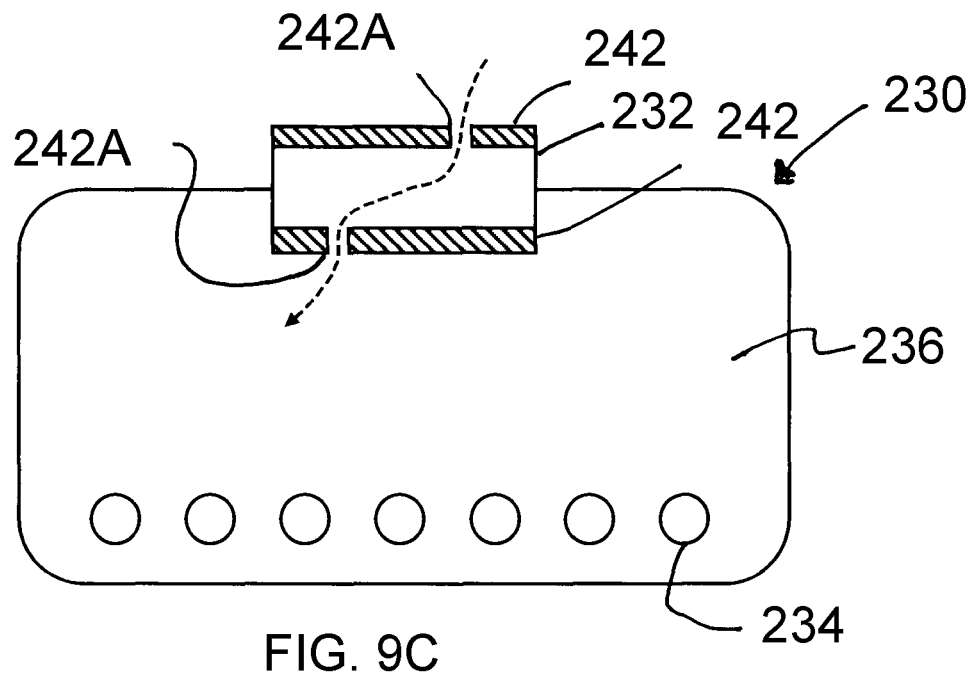
FIGS. 9C and 9D show another variation of the valve of FIG. 9A comprising catheter passage holes.
Figure 9D:
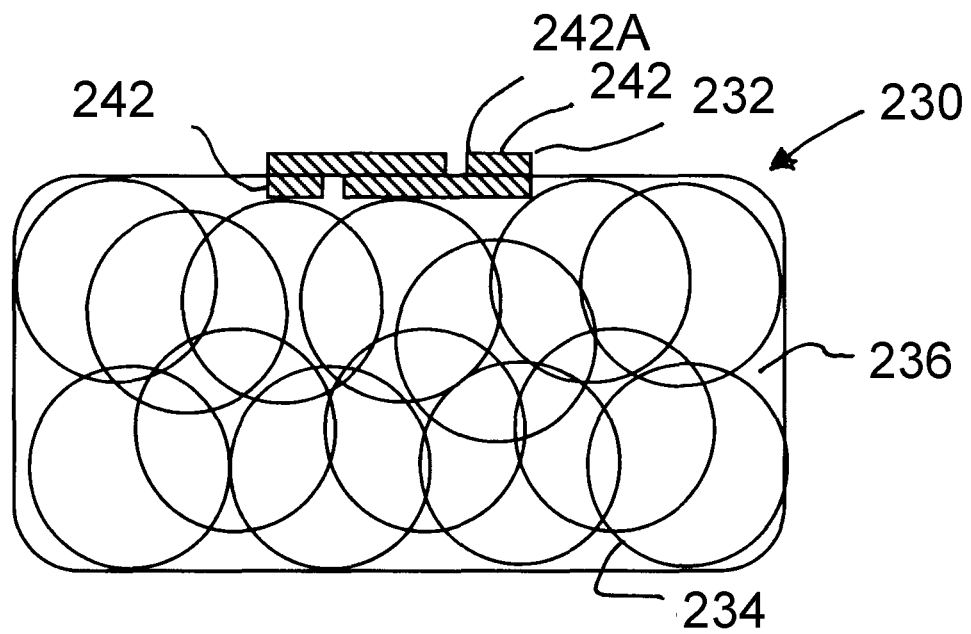

Similarly, in variations in which the filler material is a fluid or slurry material that is delivered to the reservoir by a conduit or catheter, each of two fluid impermeable may be punctured by catheter passage holes 242A, as illustrated in FIG. 9C, to create permeable regions to allow the catheter, not illustrated, to be threaded from the exterior of the device to the interior of the device when the device has no filler material in the reservoir. The path of the catheter is illustrated in FIG. 9C by the dashed arrow. FIG. 9C illustrates this variation of the valve schematically in the "open" configuration that would obtain immediately after deployment but before the filler material was hydrated and FIG. 9D shows the same valve after the filler material is fully hydrated and the conduit has been extracted. As shown in the figures the gap between the two layers in FIG. 9C is pushed closed in FIG. 9D by the pressure of the filler material in the reservoir. This closing pressure occurs with both hydrated swellable filler material, as illustrated, and when the filler material is just a fluid pumped into the reservoir under pressure.

Figure 9E:
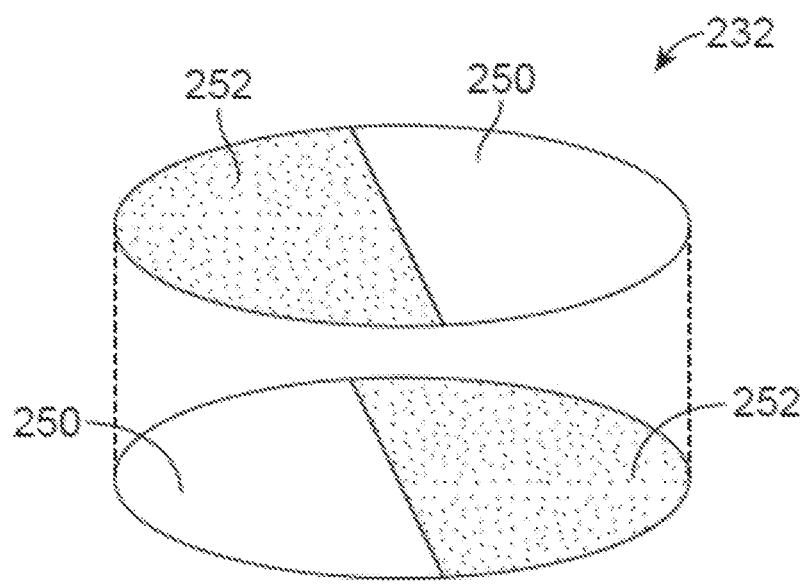
FIG. 9E shows a variation of a valve comprising demi-lunar hybrid flow control layers in which the impermeable region and permeable region are semicircular.

FIG. 9E show another variation of a valve 232. In this example the valve 232 comprises more than one layer. As shown, this hybrid valve 232 comprises two demilunar hybrid flow control layers 240, each of the layers having a hybrid construction being permeable in some generally semi-circular (viz., demilunar) regions 250 and impermeable in other regions 252. The impermeable regions 252 of one layer are at least complementary to the permeable regions of the second layer; that is, where one layer has a permeable region the other layer has an impermeable region; generally there will be regions in which both layers are impermeable. Examples of the materials include a permeable patch comprising a polyester mesh and an impermeable semicircular patch comprising latex.

As illustrated in FIG. 9E, hybrid valve 232 comprises two substantially identical demilunar hybrid flow control layers, one on top of the other, wherein the two layers are oriented so that impermeable region 252 of a first hybrid control layer is aligned with the fluid permeable region 250 of a second hybrid flow control layer. By symmetry, impermeable region 252 of second hybrid flow control layer is aligned with the fluid permeable region 250 of first hybrid flow control layer. The two layers are affixed, typically with glue, around their periphery only, thereby allowing the central areas of the two layers to move apart freely.

In these exemplary embodiments of a hybrid valve, the flow control layer disposed on the internal side of the valve preferably can also function as filler material containment layer, with containment being achieved by the mesh comprising permeable patch. Alternatively, a separate innermost filler material containment layer must be added to the assembly.

In other embodiments, hybrid flow control layer is fabricated by joining a patch of permeable material and a patch of impermeable edge-to-edge, wherein the joint may be a butt joint, for example, or a lap joint, for a second example, wherein further the outer periphery of the edge-joined materials is designed to fill or cover orifice. In another exemplary embodiment of a hybrid valve the skin itself can serve as one of the flow control layers.

Figure 10A:
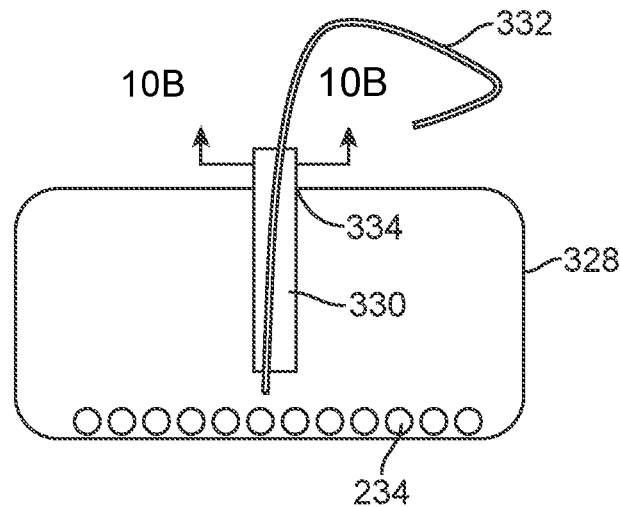
FIG. 10A illustrates a variation of a tunnel member as discussed above that forms a sealable fluid path preventing material from escaping from the interior of the device.

In another variation, the devices described herein can include a self-closing tunnel member. FIG. 10A is a schematic illustration of a variation of a tunnel member as discussed above. As shown, the tunnel member forms a fluid path that effectively seals and prevents material from escaping from the interior of the device. In some variations, the effective seal is caused by the nature of the layers of the tunnel member to close together and occlude any lumen extending therethrough. The interior layers that form a lumen in the tunnel member can join together and reduce the effective diameter of the lumen to increase a resistance to fluid flow through the tunnel member. Alternatively, or in combination, one or more substances can be positioned within the tunnel member lumen, where the substances increase the resistance to fluid flow. For example, the substances can expand to further reduce the effective diameter of the lumen, and/or the substance can stick together to increase a force required to open the lumen. As shown in FIG. 10A, the tunnel member can extend within the device as well as outside of the device. However, variations include valves in which one of the two ends is flush with the skin of the device or in which the valve is totally within the reservoir but is attached to an inwardly formed nipple to complete the fluid path between the exterior and interior of the device.

FIG. 10A illustrates an example of a device with a tunnel member forming the sealable fluid path. As shown, the device assembly contains a tunnel body/valve 330 comprising a liquid impermeable material that can be securely joined to the skin 328 in any manner conventionally known or by those discussed herein (including, but not limited to gluing, welding, heat sealing, or other means). Examples of materials useful for the tunnel member include polyurethane, nylon-12, and polyethylene. The tunnel member 330 can include any number of fluid transport members 332. In the illustrated variation, the valve is coupled to a conduit. However, variations include a wick type device located within the tunnel member.

Figure 10E:
FIG. 10E shows the tunnel in its closed configuration after the conduit is removed.
Figure 10B:
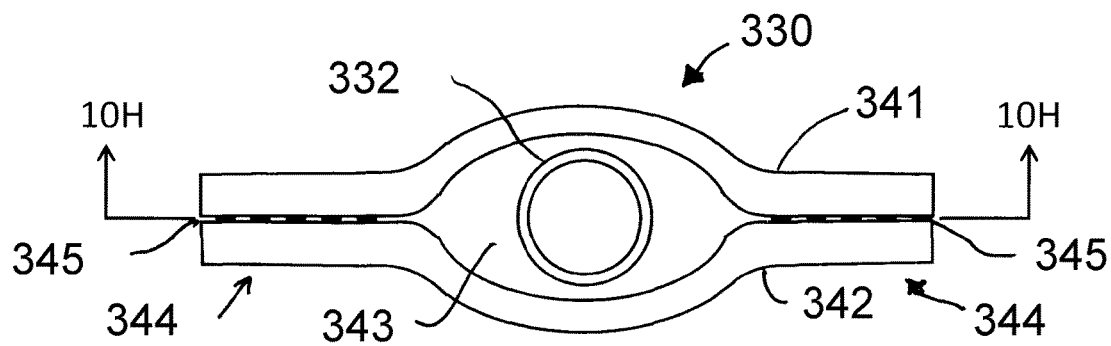
FIG. 10B shows a schematic cross sectional view of tunnel taken along line 10B-10B of FIG. 10A.
Figure 10C:
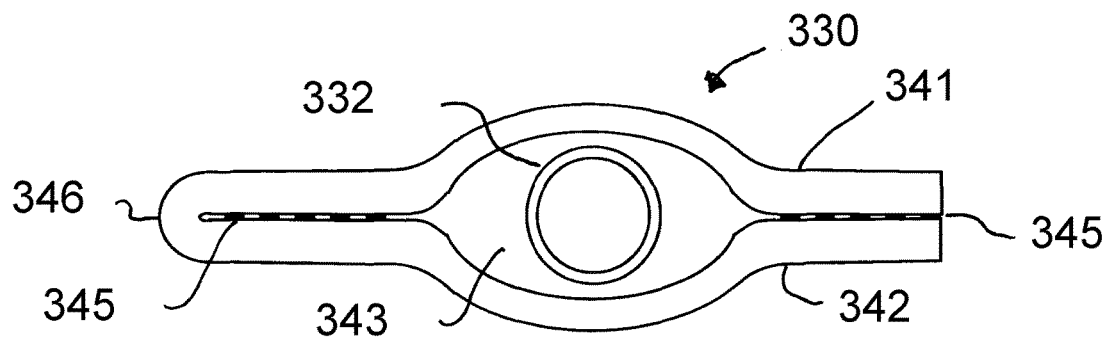
FIGS. 10C and 10D show schematic cross sectional views of two variations of the tunnel member of FIG. 10A
Figure 10D:
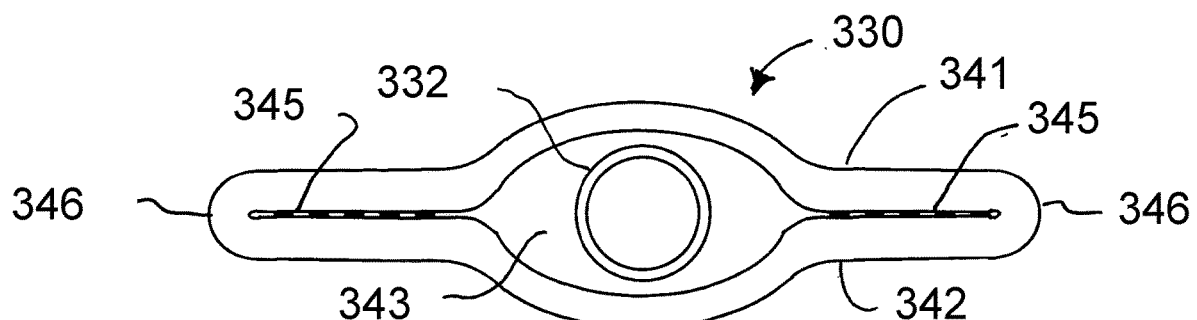

FIGS. 10B-10D show a cross sectional view of tunnel body or tunnel member 330 taken along line 10B-10B of FIG. 10A. As shown in FIG. 10A, the tunnel body 330 forms part of the fluid transport member 332 allowing transport of fluids between the interior/reservoir and interior of the device assembly. In general terms tunnel member 330 comprises, for example, an upper layer 340 and a lower layer 341 that are sealed together along their longer edges but are left unsealed along an axial central region. The unsealed region forms a lumen 343 that extends along the tunnel member so that the lumen can extend from the end of the tunnel member that is exterior of the device through to the end of the tunnel member that is located within an interior reservoir of the device. The lumen permits delivery of a fluid into the device through any of the variations described herein. For example, the device can use a wick or a fluid transport member to pass fluid from the exterior of the device into the interior reservoir. In some variations the fluid transport member may be pushed through the lumen by spreading the layers apart. In certain variations, the fluid transport member 332, can be detachable from the tunnel member 330. Upon removal of the fluid transport member 332, as shown in FIG. 10E, the layers of the tunnel member 330 move toward each other to effectively close the central lumen 343 to an extent that the tunnel member effectively seals and prevents migration of the filler material from the reservoir. In certain variations, the layers of the tunnel member will not be fully closed, however, the tunnel member will still prevent fluid flow therethrough. In additional variations, the inherent flexibility of the tunnel member will prevent fluid from migrating through the lumen out of the reservoir. Furthermore, the pressure within the reservoir pressing on the outer surface of the tunnel member acts to increase the resistance to fluid flowing within the lumen of the tunnel member.

This self-closing behavior (that is, the closing behavior is initiated and completed without any external force, stimulus, energy, or action beyond the removal of the fluid transport member 332) is effected by one or more physical mechanisms. In some variations the mechanism is the natural elasticity of the layers of the valve working to restore the layers to their initial, flat, in-contact condition. In other variations the pressure of the filler material in the reservoir presses the layers, which were held apart by the fluid transport member, together.

One variation of the tunnel member, illustrated in FIG. 10B, includes an assembly formed by two discrete membrane layers, the upper layer 341 and the lower layer 342, that are joined by gluing, welding, heat sealing, or other means along their two edge regions 344 as indicated by bond line 345. In another variation, illustrated schematically in FIG. 10C the assembly may be formed by a single membrane that has been folded in half with a fold 346 that is parallel to central lumen 343, wherein again the two regions parallel to and bordering central lumen 343 are joined together by gluing, welding, heat sealing, or other means. In some variations RF welding has been used. After the joining process is complete, the material in fold 346 may be cut away or otherwise removed or it left in place. In a third variation, shown schematically in FIG. 10D the assembly may be formed by a sleeve of membrane material, for example, fabricated by extrusion. Flattening the sleeve creates an assembly with the two desired layers. The central lumen can be formed by again joining together the two regions parallel to the lumen by gluing, welding, heat sealing, or other means and again, after the joining process is completed, the thusly created two folds 346 may be left in place or removed. Functionally these variations of the tunnel member are equivalent and the choice of fabrication approach will be determined as an engineering decision.

In exemplary tunnel members the layers can typically be between 0.001 inch or less and 0.1 inch thick. In one example a tunnel member includes a single layer thickness of 001 inch. One suitable layer material is a 0.001" thick, high tack urethane film.

In some variations the tunnel member has a length (parallel to the central lumen) of between about 0.5 inches and 2.75 inches and a width of between 0.25 inches and 0.75 inches, although both larger and smaller tunnel members are possible. The central lumen runs the full length of the tunnel member and has a width, in one variation, of 0.095 inches, where the width is a design choice determined by the size of the particular fluid transport member 332 selected.

In additional variations, tunnel members can be flexible, compressible and/or deformable. In additional variations, the lumen between the layers of the tunnel member can be reopened after fluid transport member has been removed by the insertion and passage of a structure (e.g., a conduit or other fluid transport structure) through the closed tunnel member.

As noted above, the tunnel member allows for detachment of the remainder of the fluid transport member at any time, but typically once a sufficient amount of fluid is delivered to the device. Removal can occur via applying tension to a portion of the fluid transport member. Variations of the tunnel member can employ permeable membranes, filter, or valves placed at the end of the tunnel member to prevent dry hydrogel or other filler materials from entering the tunnel and affecting the ability of the tunnel member to seal. In some embodiments, the membrane or filter may comprise a permeable fabric such as polyester, nylon, or cellulose. In other embodiments, a valve is placed at the end of the tube comprised of a one-way duckbill or umbrella valve (available from MiniValve of Oldenzaal, Netherlands). Alternatively, or in addition, filler material 234 can be contained in an inner container which prevents the filler material from entering the tunnel member and swelling upon infusion of liquid, thereby clogging the valve.

Figure 10F:
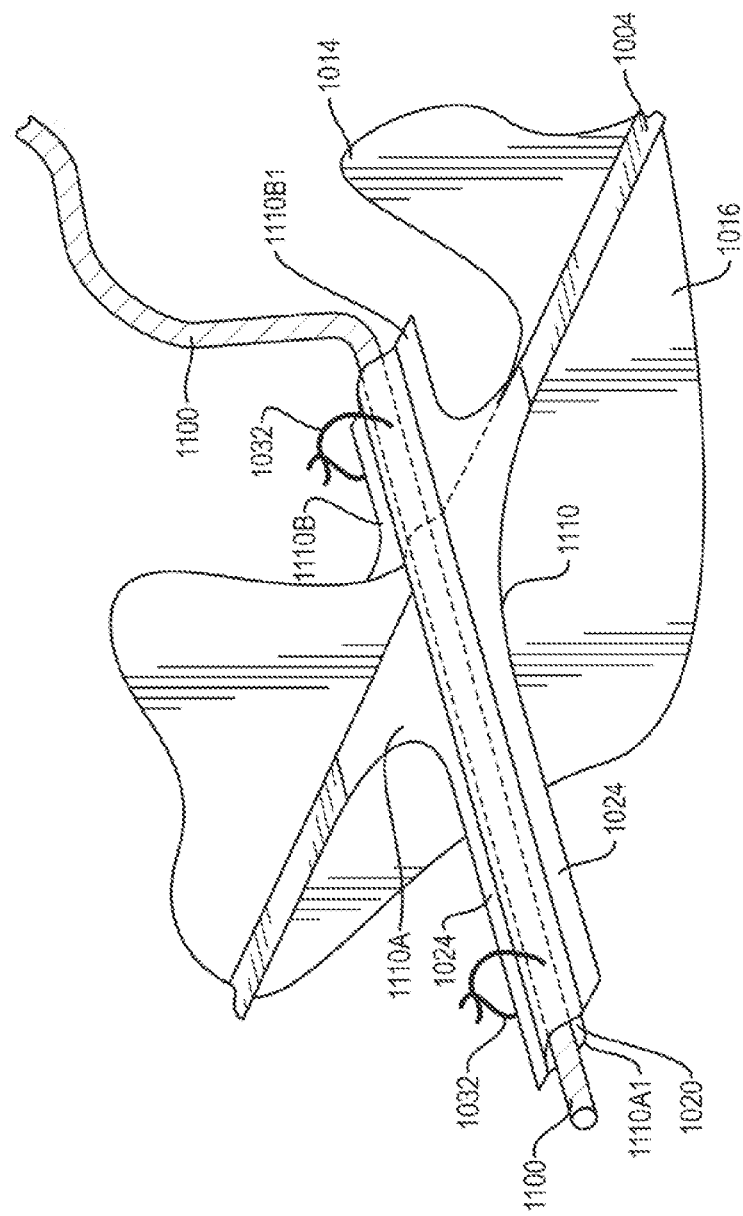
FIGS. 10F to 10I show a conduit that is mechanically coupled to a tunnel member.

Referring to FIG. 10F, tunnel member 1110 comprises an interior section 1110A, which section is disposed inside the device assembly, and an exterior section 1110B that extends outwardly from the exterior of the skin. Interior section 1110A comprises an internal end 1110A1, which is fabricated from flexible membrane-like materials. Once the device assembly is fully expanded, conduit 1100 is withdrawn from lumen 1020 from outside the device assembly. In some circumstances the drag between the conduit and the walls of the lumen as the conduit is withdrawn may result in interior section 1110A "accordioning" or folding itself against the walls of the device. In some variations interior section 1110A of the tunnel member is attached to an interior surface of the device body to prevent such folding. In some variations the attachment is achieved by fastening internal end 1110A1 to either upper material surface 1014 or lower material surface 1016. In one variation a chemical bond or spot of glue is employed. The glue spot is disposed near to internal end 1110A1 but in such a manner to avoid accidentally obstructing orifice 1020; for example, the glue spot may be disposed 2 or 3 millimeters away from internal end 1110A1. Tunnel member 1110 is rotated about seam 1004 until internal end 1110A1 touches the material surface. Tunnel member 1110 and the material surface should both be smooth and flat during this gluing operation.

In additional variations, as shown, for example, in FIG. 10F, a portion of the tunnel member extends outside the device assembly to form an external section 1110B. In some variations, as shown in FIG. 10I, external section 1110B terminates with two unjoined flaps, upper flap 1028 and lower flap 1026, which may be extensions of upper layer 341 and lower layer 342 respectively. In other variations external section 1110B may comprise a single flap or layer of material. In some examples, external section 1110B is typically between 0.1 inch and 0.5 inch long. As will be discussed below with reference to FIG. 11, in some variations the layers of the tunnel member are fabricated as integral parts of the upper and lower skins of the device. In these variations there is no material available to form the upper and lower flaps as extensions of the upper and lower layers, in which case a free-standing external upper flap 1028 and/or lower flap 1026 may be attached to the external surface of the device using any convenient joining method, for example, gluing or they may be attached in the seam. The free-standing flap or flaps are joined to the device in close enough proximity to the tunnel member to be able to touch a fluid transport member disposed through the central lumen of the tunnel member.

In some variations the tunnel member comprises retaining elements to releasably hold the conduit in place throughout deployment of the device assembly. FIG. 10F illustrates one embodiment for retaining the conduit in a partial cut-away view from the interior of the device assembly. tunnel member 1110, as described above, is typically formed by sealing the edges of two layers of membrane material to form sealed seams 1024. In some variations sealed seams 1024 extend all the way to an external end 1110B and/or internal end 1110A1 while in other variations the edges of the two layers may be unsealed for some length inward from external end 1110B and/or internal end 1110A1. The relative lengths of the interior and exterior sections of tunnel member 1110 have been distorted in the figure for clarity purposes. Typically exterior section 1110B is just long enough to accept conduit 1100. As has been discussed, conduit 1100 is inserted through orifice 1020 prior to deployment of the device assembly and is used to deliver fluid to the reservoir therein to expand device assembly. Conduit 1100 must remain disposed in tunnel member 1110 until enough fluid has been delivered to the device assembly to make it too large to inadvertently pass through the pylorus while at the same time conduit 1100 must be removable from the device assembly once its deployed profile has been achieved. Further, it is desirable that conduit 1100 also be useful for retrieving the device assembly from the stomach or esophagus in the case of an aborted deployment. In such an aborted deployment the conduit must be held in the tunnel member with enough resistance to withstand the drag on the unexpanded device assembly as it is retrieved upwardly through the esophagus.

A suture 1032, which may be inserted through either or both of interior section 1110A or exterior section 1110B, is designed to hold the conduit in the tunnel member under a wide range of extractive force. As illustrated in the figure, suture 1032 is stitched through the two layers of the tunnel member, simultaneously passing through conduit 1100. The suture is tied to itself on the exterior of tunnel member 1110. The small punctures in conduit 1100 and tunnel member 1110 through which the suture passes are too small to allow any significant loss of liquid filler.

Once the device assembly has assumed its deployment profile conduit 1100 must be withdrawn from tunnel member 1110. Conduit 1100 is released from tunnel member 1110 by the controlled, on-demand degradation of suture 1032. As is discussed above certain suture materials can be dissolved or structurally weakened by exposure to specific exogenous agents not normally in the gastric environments, or not in the gastric environment in high enough concentrations to degrade the suture during the deployment time period. For example, poly(caprolactone) [PCL] softens, melts, and weakens above a pre-determined temperature, $T_M$. In some cases the pre-determined temperature can be designed to be greater than normal body temperature but lower than human's physiologic pain threshold. In such a case, a PCL suture can be degraded by infusing heated liquid (above $T_M$) through conduit 1100 at the end of the deployment period or by having such liquid consumed orally.

In order to avoid over-filling the device assembly when the heated liquid is infused through the conduit the hot liquid infusion must start at after a pre-determined volume of un-heated liquid filler material has been infused, where the known capacity of the device assembly, the volume of fluid residual in the conduit, and the thermal capacity of the system are all incorporated into the determination. It should be noted that if the initial infusion of hot liquid fails to release the conduit by melting the suture, liquid can be withdrawn up the conduit to slightly reduce the volume of the device assembly and a second charge of hot liquid infused.

Figure 10H:
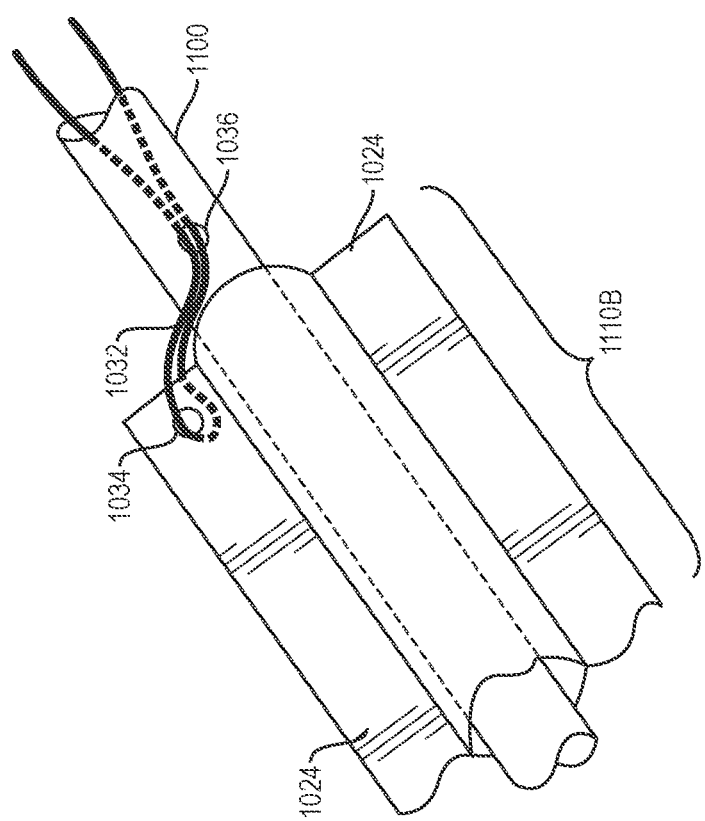
Figure 10G:
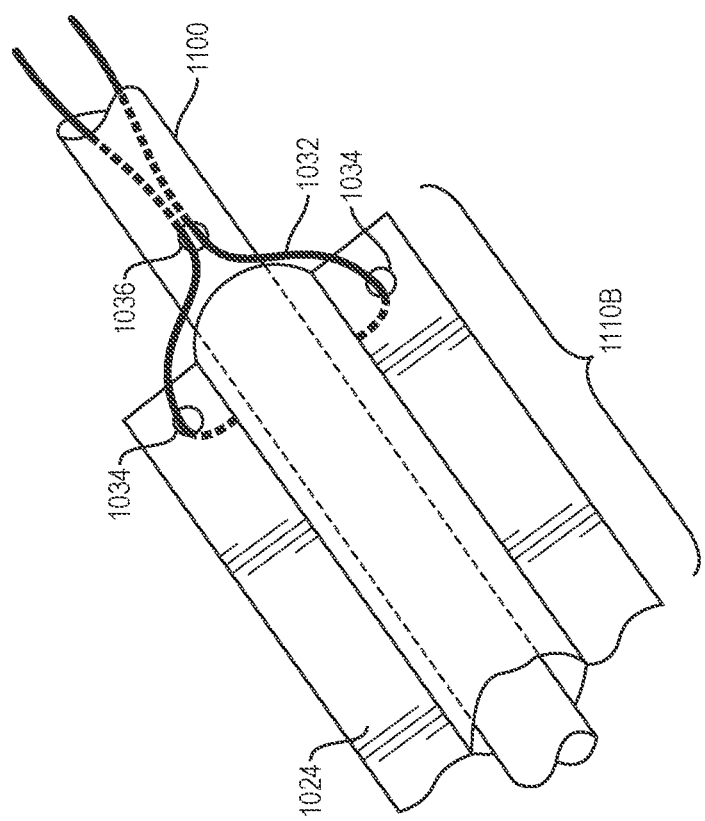
Figure 10I:
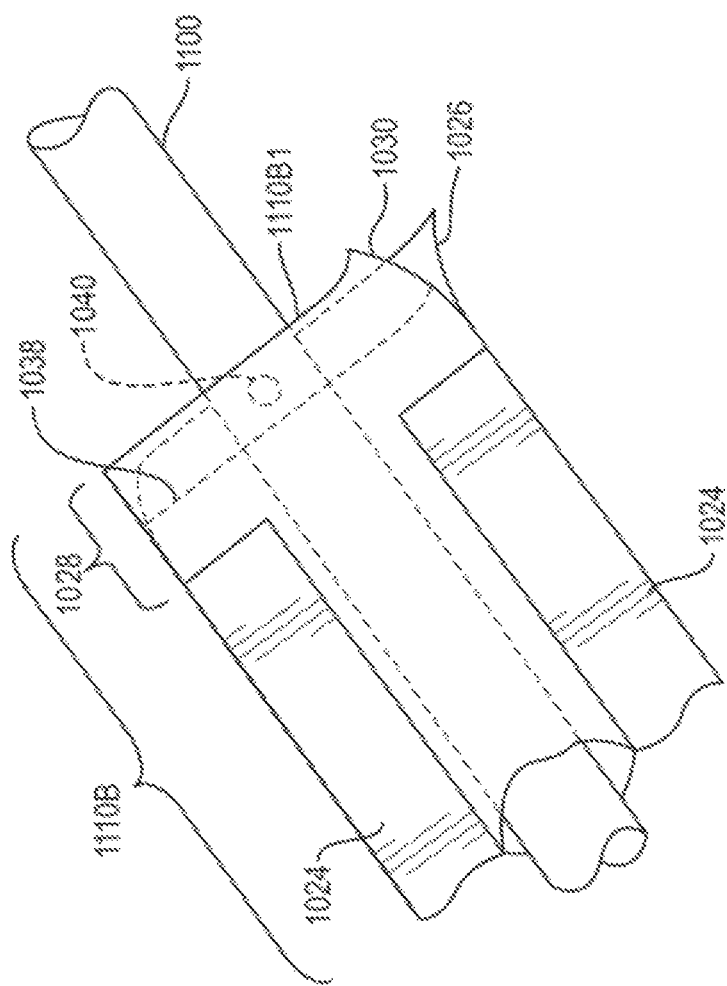

In another variation, as depicted in FIG. 10G and FIG. 10H, conduit 1100 is detachably joined to one or both double layer sealed seams 1024 of tunnel member 1110 with a loop of suture material 1032. Suture loop 1032 comprises a single long loop which starts and ends at the external (e.g., patient's mouth) end of conduit 1100. The loop starts at the external end, runs down the interior of conduit 1100, and exits the conduit at a small orifice 1036 that transverses the wall of conduit 1100 near the proximal end of exterior section 1110B. After exiting from orifice 1036, the suture passes through one or two eyelet holes 1034 in sealed seams 1024 before returning to orifice 1036. The suture completes its loop by running back up the interior of conduit 1100. The two ends of suture loop 1032 are retained at the external end of conduit 1100.

Suture loop 1032 is installed during the manufacture of the device assembly and remains disposed in conduit 1110 during infusion of the liquid filler material. Conduit 1110 cannot easily be pulled out of tunnel member 1110 while suture 1032 is in place. Once the device assembly has assumed its deployment profile, one end of suture loop 1032 may be released while the other end of the loop is pulled outwardly. When at least half the length of suture forming suture loop 1032 has withdrawn from conduit 1100, the loop is known to be unthreaded from the eyelet hole(s). Freed from the eyelets, conduit 1100 can then be withdrawn from tunnel 1100.

In some embodiments suture loop 1032 of FIGS. 10G and 10H may be made from PCL, in which case conduit 1110 may also be released by melting suture loop 1032 through the infusion or ingestion of hot liquid, as described above.

Another variation of fluid transport member 1100 is illustrated in FIG. 10I. In this variation sealed seams 1024 stop short of external end 1110B, leaving two flaps of material, upper flap 1028 and lower flap 1026, where upper and lower are arbitrary designations relating only to the figure. Upper flap 1028 or lower flap 1026 is prepared with a release region in the form of a rip-off tab 1030 which comprises the most proximal section of upper flap 1028 and which is distinguished as the region sectioned off by a tear line 1038 of diminished tear-strength material. The tear-strength of tear line 1038 may be reduced, for example, by perforations, physical thinning, or chemical application (e.g., partial de-polymerization). In some variations the tear-strength of tear line 1038 is between 1 and 1.5 lbs. while other variations may have tear-strengths between 0.5 lbs. and 2.5 lbs.

In some variations the length of flaps 1028, 1026 is approximately 0.5 inches and tear line 1038 is disposed approximately 0.3125 inches from the exterior surface of the device.

As illustrated in the figure, conduit 1100 is attached to rip-off tab 1030 at spot location 1040, which is on the external side of tear line 1038, where such attachment may be accomplished, for example, by gluing, melting, or ultrasonic welding. In some variations the attachment point, spot location 1040, is at least 0.0625 inches away from tear line 1038. In this variation conduit 1100 is detached from tunnel member 1110 by pulling outwardly on conduit 1100 with enough force to separate rip-off tab 1030 from upper flap 1028 along tear line 1038. Although depicted examples show only a single rip-off tab 1030, additional variations include two or more rip-off tabs, one such tab on each of the two flaps, wherein conduit 1100 is attached to both tabs.

Figure 10J:
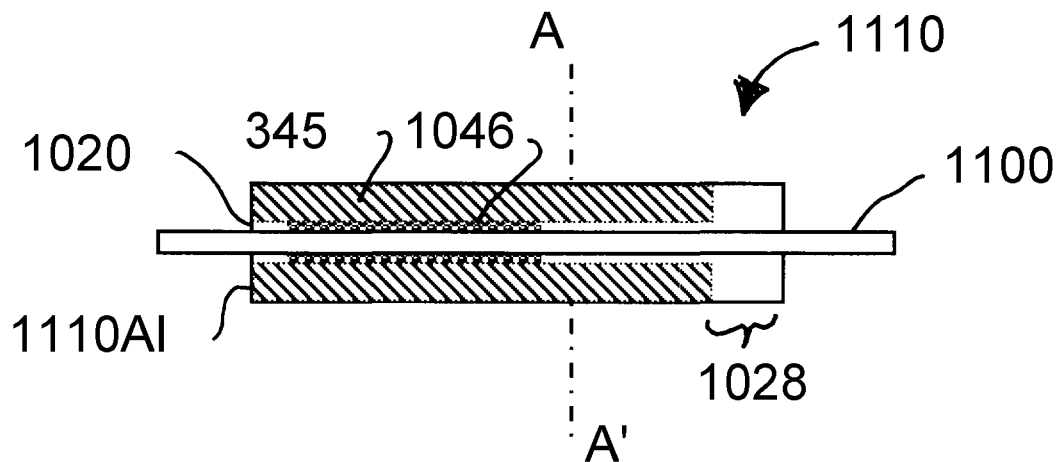
FIG. 10J to 10L show a schematic cross-sectional view of a tunnel member including a tunnel substance between layers of the tunnel member and a conduit taken along line 10H-10H of FIG. 10B
Figure 10K:
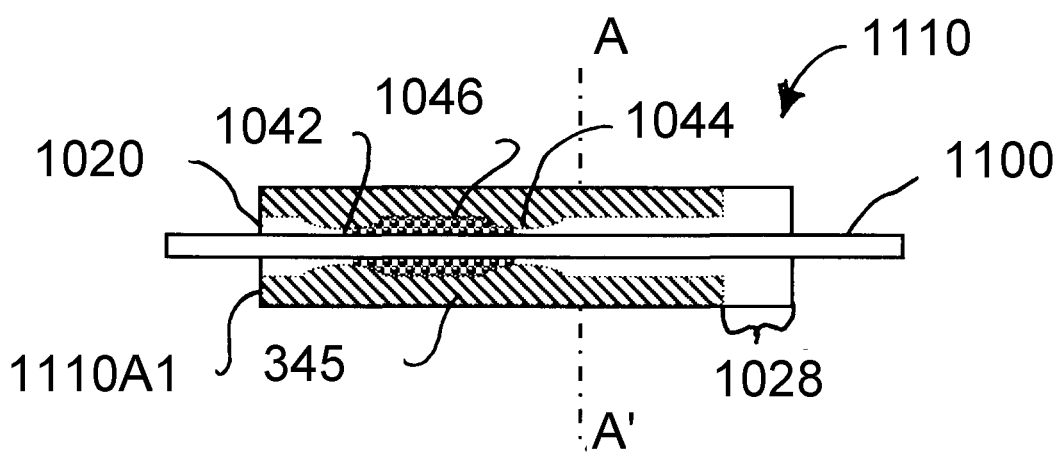
Figure 10L:
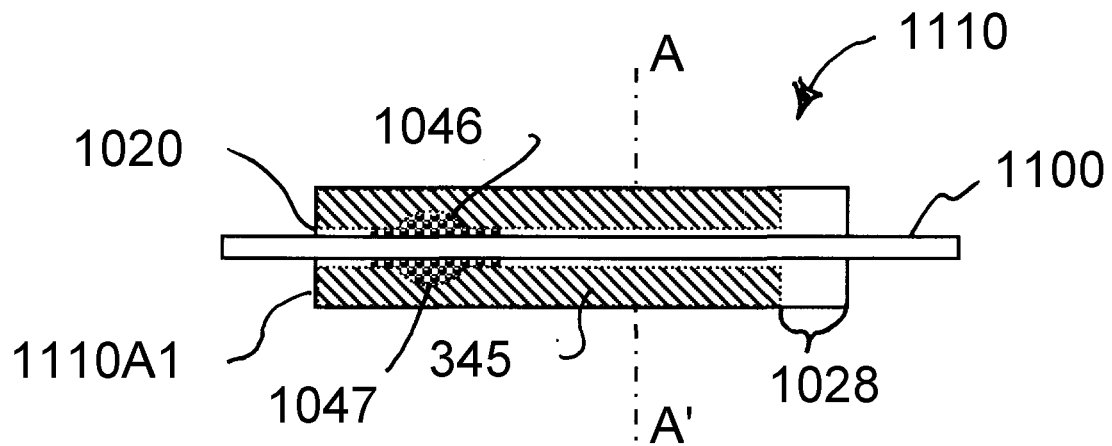

In some variations, as depicted in FIGS. 10J-10L, which show a cross sectional view of tunnel member 1110 taken along line 10H-10H of FIG. 10B, the deposition of a tunnel substance 1046 between the layers of the tunnel member may enhance the sealing effectiveness of tunnel member 1110. In some variations tunnel substance 1046 is a hygroscopic, fluid swellable material. In these variations the swellable material generally remains unswollen while the conduit 1100 is installed in the valve. After conduit 1100 removal, swellable material 1046 intercepts any liquid or semi-liquid filler material from the reservoir that migrates between the two layers of the nominally sealed valve. The swellable material swells in response to any liquid component in the intercepted filler material, thereby blocking further filler material migration through the valve. The substance can also serve as a packing material within the tunnel member. Additional variations include a tunnel substance that is hydrophilic.

The swellable material 1046 is typically superabsorbent poly(acrylic acid) hydrogel granules or superabsorbent poly(acrylic acid) hydrogel fibers. The swelling ratio of these substances (the mass of water absorbed for every gram of substance) is typically greater than 10.

In other variations the tunnel substance 1046 is a low-solubility material. Such a low-solubility tunnel substance can also function as a lubricant. In one example, the tunnel substance comprises a bio-compatible grease or grease-like material. The tunnel substance can be selected to have a high enough viscosity to remain in the central lumen for the expected duration of deployment. Typically the material is not soluble in water to any significant degree. In some variations the material is a high viscosity silicone grease. Additionally, the tunnel substance can be a hydrophobic material.

In some variations, the substance 1046 is inserted into central lumen 1020 prior to the insertion of conduit 1100 while in other variations the tunnel substance is injected into the lumen and around the conduit after the conduit has been inserted through the lumen.

As illustrated schematically in the cross-sectional view in FIG. 10J, central lumen 1020 has a diameter over most of its length that closely matches the diameter of conduit 1100. This snug fit reduces the leakage of filler material during the filling process since filling material in the reservoir can enter the internal end 1110A1 of the lumen in the space around the exterior of the conduit. The dashed line A-A' indicates the skin of the device assembly. Generally tunnel substance 1046 is disposed toward the internal end of valve 1110 although in some variations it may be disposed towards the proximal end of the valve in the region approaching but not including the region of the unjoined flaps, as shown in the cross-sectional figure as upper flap 1028.

As depicted in the cross-sectional view schematically in FIG. 10K, in some variations lumen 1020 is tapered in one or more regions 1042, 1044. The region between the two tapered regions forms a pocket into which the tunnel substance may be disposed. In embodiments with only one tapered region the region will typically be disposed near internal end 1110A1 and the tunnel substance 1046 will be disposed to the proximal side of the tapered region. Tapered regions 1042 and 1044, may have a design diameter so that the conduit 1100 fits snugly through the tapered regions and less snugly in the untapered regions. That is, the diameter of the tapered regions is substantially equal to the diameter of the conduit. The tapered region can then prevent most of the liquid filler from reaching the tunnel substance while conduit 1100 is in place, inhibiting any swelling of a swellable tunnel substance or any migration of the tunnel substance out of the lumen during storage. This variation is particularly suitable for a swellable tunnel substance, which in many variations comprises dry, flowable granules. Once the conduit is removed any fluid that follows the conduit up the lumen is intercepted by the swellable material which then swells and blocks the flow of additional fluid.

Another variation is illustrated schematically in the cross-sectional view in FIG. 10L. In this variation lumen 1020 comprises an enlargement region or pocket 1047 into which an extra volume of tunnel substance 1046 may be inserted. This variation is similar in function to the variation illustrated in FIG. 10K. It may be advantageous compared to that variation in that the diameter of the lumen may be snugly fit to the catheter over a longer length than is possible in the variation of FIG. 10K, thus providing better containment of the tunnel substance in the pocket and greater resistance to filling fluid flow out of the reservoir.

Figure 10M:
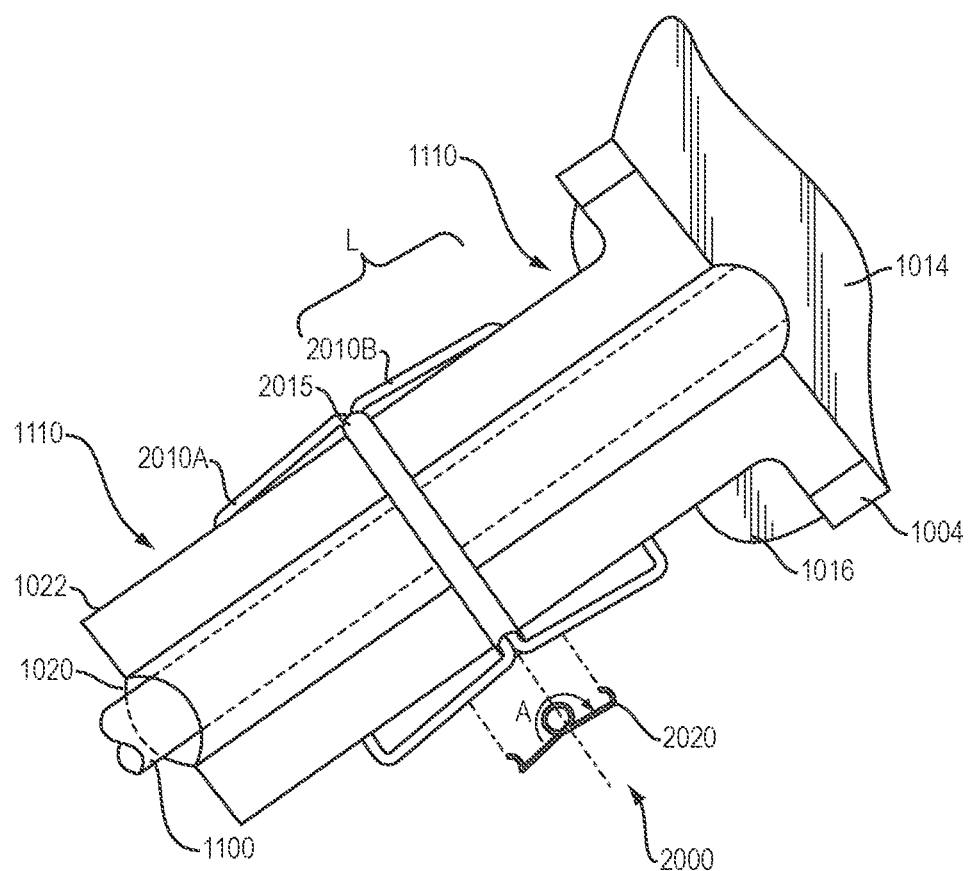
FIGS. 10M and 10N shows the use of a spring loaded closure device that aids in sealing of a tunnel member.

In some embodiments the seal of valve 1110 may be enhanced mechanically, as illustrated in FIG. 10M. In this exemplary embodiment a spring-loaded closure device 2000 is disposed on elongate portion 1022 of valve 1110. Closure device 2000 comprises two, U-shaped loops 2010A, 2010B, loops 2010 in this exemplary embodiment being connected at a hinge axle 2015. Each loop 2010 comprises a width comparable to the width of elongate portion 1022 and a length, L, which is the length of each loop 2010 extending from hinge axle 2015. For clarity, the loops are illustrated with exaggerated lengths.

Device 2000 further comprises a spring 2020 or similar energy storage element. Loops 2010, hinge axle 2015 and spring 2020 are configured to allow spring 2020 to drive loops 2010 into generally adjacent alignment by rotating one or both loops around hinge axle 2015, as indicated by arrow A in FIG. 10M.

During deployment, conduit 1100 is disposed within orifice 1020, typically extending through substantially the entire length of elongate portion 1022. As previously noted, in some embodiments conduit 1100 extends beyond the end of orifice 1020, as illustrated in FIG. 10M. Closure device 2000 is disposed in its "open-flat" configuration on or around elongate portion 1022, whereby elongate portion 1022 is threaded through closure device 2000 by passing above loops 2010 and below hinge axle 2015.

Elongate portion 1022 is, by design, stiff enough to hold closure device 2000 in its open-flat configuration during deployment. It will be noted that elongate portion 1022 is stiffened during deployment by the presence of conduit 1100 since, as described herein, elongate portion 1022 is fabricated with two thin layers of a membrane-like material designed to collapse upon themselves while conduit 1100 must be rigid enough to provide an open fluid channel from a patient's mouth to his stomach.

After deployment, conduit 1100 is withdrawn from orifice 1020. Once the end of conduit 1100 passes the crossbar of loop 2010A, elongate portion 1022 is no longer stiff enough to retain loop 2010A in its open-flat configuration. Loop 2010A is rotated by torsion spring 2020 in the direction of arrow A, wrapping the distal end of elongate portion 1022 around hinge axle 2015 in the process. Loop 2010A continues rotating until it rests against loop 2010B, simultaneously pressing and sealing the doubled over elongate portion 1022.

Figure 10N:
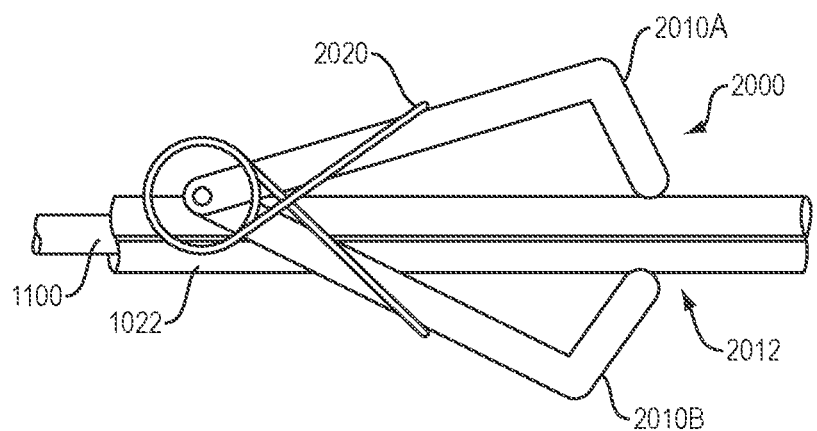

In an alternative exemplary configuration, illustrated in side-view in FIG. 10N, closure device 2000 may be used as a spring clamp only, without the doubling over functionality discussed above. As shown, during deployment closure device 2000 is disposed in its open-jaw configuration, with elongate portion 1022 inserted into an open jaw 2012 formed by loops 2010A and 2010B. During deployment conduit 1100 inside elongate portion 1022 is stiff enough to hold jaw 2012 open; when conduit 1100 is withdrawn, the force of torsion spring 2015 closes jaw 2012, sealing elongate portion 1022.

In another embodiment, not illustrated, an elastic ring provides the mechanical assistance for enhancing the seal of valve 1110. The ring is disposed around on elongate portion 1022 of valve 1110. The ring's material properties and dimensions are selected to substantially seal the tunnel member when the valve does not contain conduit 1100. However, when conduit 1100 is positioned within the tunnel member, the rigidity of the conduit resists the sealing force of the elastic ring. The elastic ring may be composed of any elastomeric material that is known to be biocompatible. Examples include silicone, polyurethane, and latex.

Figure 11A:
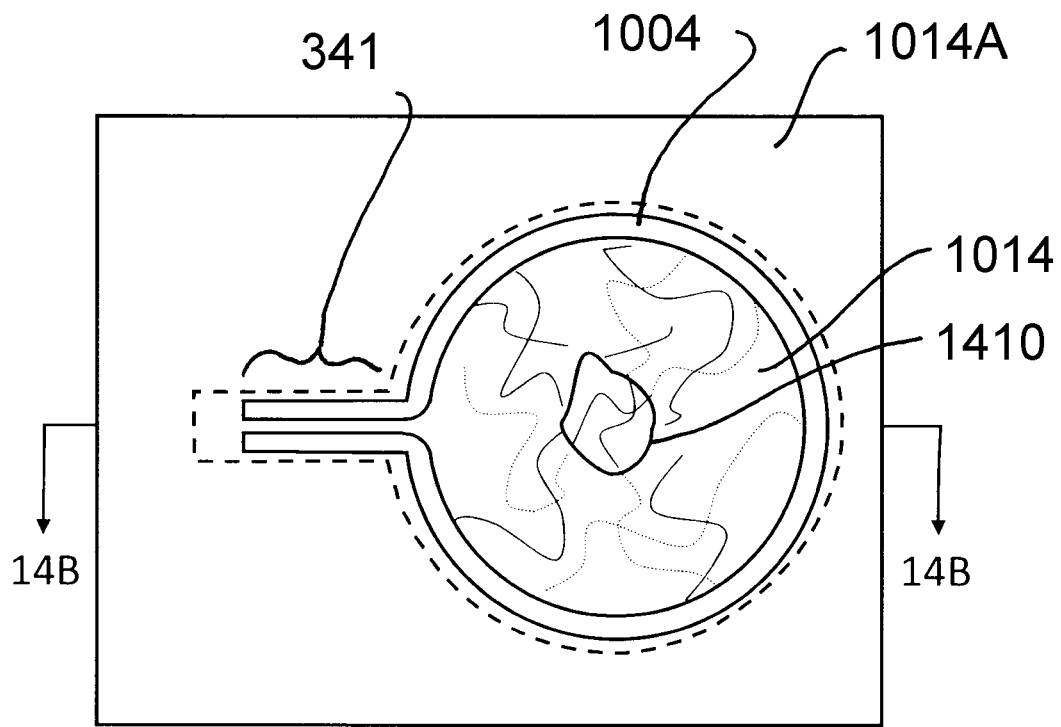
FIG. 11A is a plan view of a variation of the device in mid-fabrication in which the two layers of the tunnel member are fabricated as part of the upper and lower skins of the device.
Figure 11B:
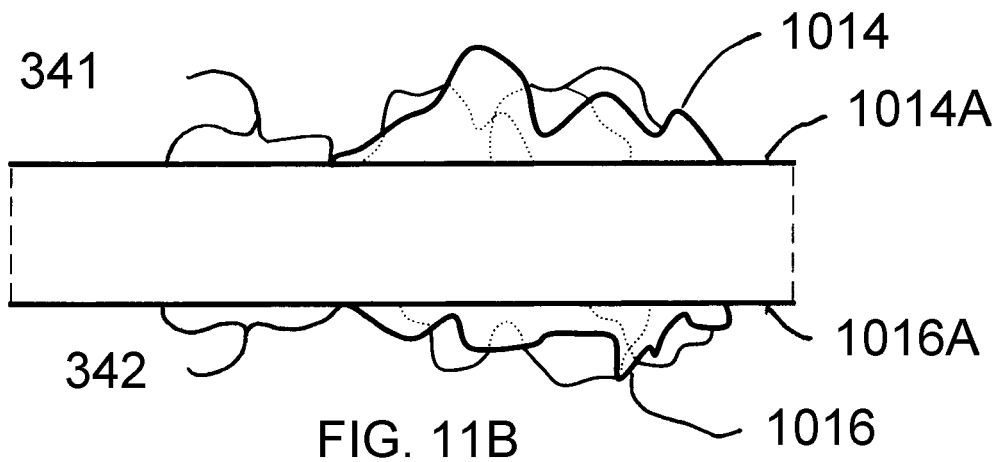
FIG. 11B is an exploded cross-sectional view of the device of FIG. 14A taken along line 14B-14B.

As was described above, in some variations of a tunnel member the two layers of the valve, upper layer 341 and lower layer 342, are fabricated as integral parts of the upper material surface 1014 and lower material surface 1016 of the device. A device having integral tunnel member layers shown in mid-fabrication in the plan view of FIG. 11A. As previously described, in a simple variation, an oblate spheroid device can be created from two pre-formed skins formed by upper material surface 1014 and lower material surface 1016, wherein upper material surface and lower material surface are sealed to each other as shown by seam 1004 was shown in FIG. 2. In one exemplary fabrication method each of the two material surfaces are thermoformed into semi-ellipsoids by heating a sheet of membrane material 1014A or 1016A in a frame and forming it over a vacuum mold wherein the mold has the desired semi-ellipsoidal shape. As illustrated in exploded cross-sectional view FIG. 11B, after cooling and upon removal from the vacuum mold, each sheet of membrane material, membrane materials 1014A or 1016A, retains the semi-ellipsoidal shape of upper material surface 1014 or lower material surface 1016, albeit in a collapsed or crumpled form, the membrane material being thin and flexible. It will be noted that each formed sheet has a preferred interior surface 10141, 10161 and a preferred exterior surface 1014E, 1016E, where the interior surfaces comprise the concave side of the molded semi-ellipse. As illustrated in FIG. 11B, the two sheets are disposed with their interior surfaces facing each other and in close contact, with any corresponding features aligned.

In another variation of a tunnel member, one layer of the tunnel member is fabricated as a separate membrane while the material surface of the device provides the second layer of the tunnel member. For example, lower layer 342 may be joined to upper material surface 1014 along its two edges, leaving a passage or lumen extending from the seam of the device to the internal end of lower layer 342.

The two sheets are then joined around the periphery of the semi-ellipses to seal them together along sealed seam 1004. One method for sealing the device 1000 comprises an ultrasonic or radio-frequency (RF) weld. In the example shown in FIG. 11 the device includes a tunnel member in which the two layers of the valve are integral to the upper and lower material surfaces. As shown in FIGS. 11A and 11B, the integration of the valve upper layer 341 and lower layer 342 into the device surface material can be accomplished by configuring the joining, welding, or gluing fixture to form a pair of seams projecting in an outwardly radial direction relative to the nominally circular seam around the material surfaces. These projecting seams are formed in a flat region of the membrane material and are disposed generally parallel to each other and spaced by a gap substantially equal to the desired diameter of central lumen.

After joining the device is trimmed to remove the excess material along a trim line 1006. Either before or after joining an access aperture 1410 is opened in one of the material surfaces. Typically this aperture is circular although it appears distorted in FIG. 11A due to the crumpling of upper material surface 1014. As will be understood, when the device is inverted by pulling the lower material surface 1016 through aperture 1410 to put seam 1004 on the interior, the outwardly projecting tunnel member formed by upper and lower layers 341 and 342 is converted into the desired inwardly directed valve.

Delivery System

Figure 12:
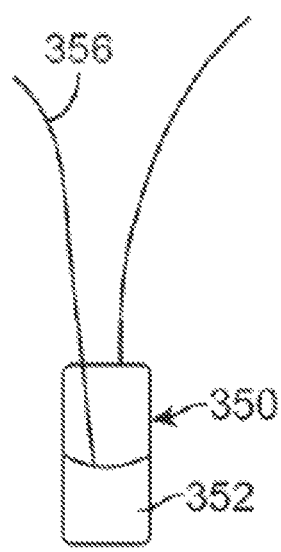
FIG. 12 shows a device assembly compressed to fit within an oral dosage form such as a pill, capsule, sleeve, or other form that enhances the ability of positioning the device via ingestion or swallowing without the aid of another medical device.

As shown in FIG. 12, in certain variations, the device assembly can be compressed to fit within an oral dosage form 352 such as a pill, capsule, sleeve, or other dosage form that enhances the ability of positioning the device via ingestion or swallowing without the aid of another medical device. In such a case, the device 350 is contained within the oral dosage form 352 and can optionally include a tether 356. It should be noted that the conduits described above can also be used as a tether or vice versa. In any case, the tether 356 allows for controlling the deployment location of the device 350 within the gastrointestinal tract by manipulation of the tether 356, and finally completing the administration procedure by releasing control of the device 350, either by releasing the tether 356 for the patient to swallow or, more typically, by detaching the tether from the device 350 or oral dosage form. FIG. 12 also shows a tether 356 as having two ends to allow for greater control in positioning the device 350.

In accordance with the delivery method, a medical practitioner, typically a medically trained agent such as a physician, physician's assistant, or nurse, administers the tethered, encapsulated payload to a mammal, herein referred to as the patient. The method comprises the simultaneous steps of directing the patient to swallow oral dosage form while controlling the tether. In some embodiments controlling the tether comprises the use of a tube, conduit, or catheter to transport liquid into the device, the method also includes infusion of liquid through the tube using a syringe, pump, or other liquid delivery means. Generally, the step of controlling the tether comprises, firstly, ensuring that the tether's proximal end is retained exterior to the patient and, secondly, assisting the patient by feeding the tether into the patient's mouth and throat at a rate compatible with the ingestion of the oral dosage form 352. That is, the agent typically adjusts the feed rate of the tether so the progress of the oral dosage form 352 down the esophagus is not impeded by tether-induced drag while at the same time the patient does not feel the tether is accumulating in his or her mouth. In additional variations, the medical practitioner can also use the tether by securing the section of the tether located outside of the patient's body (i.e., to a fixture in the room or to a part of the patient).

The method further comprises an optional step of controlling the delivery distance of the device. The delivery distance is, essentially, how far into the gastrointestinal tract the device is permitted to travel. Typical devices are designed to be deployed in the stomach although some devices may be designed to reach only the esophagus whilst other devices can be intended to reach the pylorus or beyond. The step of controlling the delivery distance is best accomplished with a device attached to a marked tether, whereby the length of the ingested tether corresponds to the instantaneous delivery distance, which length being directly readable from a marked tether. Part of this optional step of controlling the delivery distance is stopping the further ingestion of the tether.

In certain variations, the oral dosage form 352 dissolves upon reaching the stomach and the fluids therein. Once free from the oral dosage form, the device 350 is free to expand into a deployed state or an active profile. Alternatively, device 350 expands into its active profile upon infusion of a hydrating fluid through the fluid transfer member.

One of skill in the art will note that the human GI tract is unique among the abdominal viscera as it is periodically exposed to very cold and hot substances during routine alimentation. For instance, the temperature of the stomach is known to increase to 44° C. after ingestion of a hot meal heated to 58° C. but quickly return to core body temperature (37-39° C.) in 20 minutes. Moreover, the temperature of the stomach can reach as high as 48° C. for between 1-2 minutes if 500 milliliters of 55° C. tap water is consumed rapidly (under 2 minutes) on an empty stomach. Thus, a biocompatible material that could be eliminated by melting would ideally remain stable at core body temperature (37-39° C.) but melt in response to a planned intervention that raised the temperature in the vicinity of the biocompatible material to the material's melting point. In the GI tract, such a material would have to withstand daily fluctuations in gastric temperature (e.g. after ingestion of a hot meal) and remain stable at temperatures between 37° C. and 44° C. but melt in response to a planned intervention (e.g. consuming 500 milliliter of 55° C. tap water).

In some examples it was noted that one material, polycaprolactone (PCL), has been extruded into a strong monofilament (Japanese publication JP-A05-59611 A) and has a natural melting point of 60° C., a melting point that is probably not safely usable in human stomachs. However, PCL can be modified to lower its melting point to more physiologically acceptable temperature. Moreover, the modified polymer can still be extruded into a strong monofilament suitable for suturing and stitching or a film suitable for heat welding to a membrane. PCL filamentary material with reduced melting temperatures ($T_M$) is available from Zeus Industrial Products of Orangeburg, S.C., wherein 60° C.>$T_M$>45° C. by specification.

In some variations the degradable material used as release material 106 is allowed to degrade at its natural degradation rate in the mammalian gastric environment. In other variations, degradation is triggered or effected by the intentional introduction of an exogenous substance 120. In some variations the exogenous substance is the fluid filler material delivered to the reservoir via the conduit. In these latter variations release material 106 is disposed entirely within the reservoir and is not physically contacted by the gastric environment. Further in these variations the fluid filler material both expands the device to its active profile and initiates a timed degradation of release material 106.

In additional embodiments, exogenous substance 120 is introduced orally and at least partially in a liquid format into the stomach. In the stomach, the exogenous substance 120 mixes with the resident gastric fluid to become an immersing fluid that substantially bathes the construct. Alternatively, the exogenous substance 120 may be introduced into the stomach in a solid state, as in a tablet or capsule, typically accompanied by a liquid, whereby the solid is dissolved and becomes the immersing fluid, particularly when mixed with gastric fluids. In certain embodiments extra-corporal stimulation of the exogenous substance 120 may be used.

In many variations, the release material comprises modified PCL material, either as a thin film for degradable patch or as a filamentary material. In general, modified PCL melts at a specified melting temperature, $T_M$ and the temperature of the stomach, $T_S$, remains below $T_M$. The exogenous agent for PCL, therefore, comprises an elevated temperature liquid—at temperature $T_L$—which raises $T_S$ above $T_M$. The exogenous agent temperature $T_L$ needed to raise $T_S$ above $T_M$ is based on the design details of entire system; that is, the means of delivery of exogenous substance 120, the design of release material (that is, for example, stitches, patch or knot), and the specified melting temperature, $T_M$, of the modified PCL.

For example, an intragastric construct comprising $T_M$=48° C. modified PCL will degrade after the rapid ingestion of a large volume of water with $T_L$=55° C. Clearly, the location of the PCL release material may affect the rate and/or temperature at which the PCL degrades. The extracorporal exogenous substance 120 temperature $T_L$ is higher than the melting temperature of the PCL to account for cooling of the formulation during transit to the stomach and due to mixing with the existent stomach fluids and for the placement of the release material. In one example, it was found that the rapid ingestion of approximately 500 milliliter of 55° C. water elevates stomach temperature $T_S$ to at least 48° C., high enough to dissolve/degrade the modified PCL and allow the device to open and release its hydrogel contents.

In another example, an intragastric construct comprising with $T_M$=50° C. modified PCL will degrade after rapid endoscopic infusion of 500 milliliter tap water with $T_L$=65° C., a temperature that is too hot for comfortable oral ingestion but which is tolerated by the stomach when the liquid is delivered directly to the stomach. Alternatively, the exogenous substance 120 may be delivered directly to the stomach via a nasogastric tube, again circumventing the comfort limitations of oral ingestion.

In another variation, an exogenous substance can be used to raise the temperature or otherwise change the conditions of bodily fluids to effect release of the device. Additional variations allow for the use of an exterior energy source to raise the temperature of the area surrounding the device. For example, a patient can ingest a sufficient volume of fluid, followed by the application of an external energy source (e.g., radiofrequency or ultrasound) to the exterior of the patient's abdomen to warm the fluid within the stomach to the desired $T_M$. In another variation, the exogenous substance, e.g. elemental magnesium, itself causes an exothermic reaction to occur in the stomach.

Yet another approach providing a exogenous substance 120 to an intragastric device comprising $T_M$=50° C. modified PCL is the ingestion of 500 mL of alkaline solution (e.g. saturated sodium bicarbonate) pre-warmed to 55° C. Said solution initiates an exothermic reaction upon neutralization with the stomach acid, warming the stomach contents above the 50° C. PCL melting point.

The invention claimed is:

1. A medical device for occupying a space within a patient's body and for use with a fluid delivery conduit that allows transport of a fluid into the medical device, the medical device comprising:
   a device body defining a reservoir;
   a tunnel member comprising a first open end located within the reservoir and a second open end, the tunnel member having at least two interior opposing surfaces that define a tunnel lumen extending between the first open end and the second open end;
   where the tunnel lumen is sized to slidably receive the fluid delivery conduit such that the fluid delivery conduit is slidably located within the tunnel lumen causing the at least two interior opposing surfaces to hold the fluid delivery conduit in place by friction where the tunnel member assumes an axial profile similar to a portion of the fluid delivery conduit placed therein allowing the fluid delivery conduit to transport the fluid into the reservoir, wherein upon removal of the fluid delivery conduit the at least two interior opposing surfaces of the tunnel member flatten without providing support to the tunnel member such that the tunnel member is unable to maintain a straight profile or the axial profile and bends to a second arcuate profile;
   where a portion of the tunnel member is attached to an interior surface within the reservoir of the device body to prevent folding of the tunnel member upon removal of the fluid delivery conduit; and
   a substance adjacent to the at least two interior opposing surfaces of the tunnel member, such that upon removal of the fluid delivery conduit, a cohesion of the substance causes the at least two interior opposing surfaces of the tunnel member to stick together increasing a force required to separate the at least two interior opposing surfaces and increasing a resistance to fluid flow through the tunnel lumen.

2. The medical device of claim 1, wherein the tunnel member comprises a flexible thin wall material such that increasing a pressure within the reservoir increases the resistance to fluid flow through the tunnel lumen.

3. The medical device of claim 1, wherein the substance comprises a viscous material.

4. The medical device of claim 1, where the second open end is located exterior to the device body.

5. The medical device of claim 1, wherein the substance comprises a low-solubility material.

6. The medical device of claim 5, wherein the substance comprises a bio-compatible lubricant.

7. The medical device of claim 1, wherein the tunnel member further comprises a first layer and a second layer sealed along at least a first longitudinal edge, the tunnel lumen being adjacent to the at least the first longitudinal edge.

8. The medical device of claim 7, further comprising a second longitudinal edge adjacent to the tunnel lumen and opposite to the first longitudinal edge, where the first layer and second layer are sealed along the second longitudinal edge.

9. The medical device of claim 1, further comprising an attachment that couples the fluid delivery conduit to a portion of the tunnel member extending exterior to the device body.

10. The medical device of claim 9, wherein the attachment comprises a suture.

11. The medical device of claim 9, wherein the attachment comprises a mechanical or chemical bond.

12. The medical device of claim 1, wherein a transverse dimension of the tunnel lumen is constant.

13. The medical device of claim 1, wherein a transverse dimension of the tunnel lumen varies within the tunnel member.

14. The medical device of claim 1, further comprising at least one pocket in fluid communication with the tunnel lumen where the at least one pocket is configured to retain a substance therein.

15. The medical device of claim 1, wherein the tunnel member comprises a detachable section having a region of reduced tensile strength, such that application of a tensile force causes detachment of the detachable section.

16. A medical device for occupying a space within a patient's body, the medical device comprising:
   a device body defining a reservoir;
   a tunnel member comprising a first open end located within the reservoir and a second open end, the tunnel member having at least two interior opposing flexible membranes each having a surface that define a tunnel lumen extending between the first open end and the second open end;
   a fluid delivery conduit that allows transport of a fluid into the reservoir, the fluid delivery conduit extending into the second open end of the tunnel member through to at least the first open end;
   where the tunnel lumen is sized to slidably receive the fluid delivery conduit within the second open end such that the fluid delivery conduit separates the interior opposing surfaces and where the tunnel member assumes an axial profile similar to a portion of the fluid delivery conduit placed therein allowing the fluid delivery conduit to transport the fluid into the reservoir wherein upon removal of the fluid delivery conduit the at least two interior opposing surfaces of the tunnel member flatten without providing support to the tunnel member such that the tunnel member is unable to maintain a straight profile or the axial profile and collapses to a second-arcuate profile; and
   a substance adjacent to the at least two interior opposing surfaces of the tunnel member, such that upon removal of the fluid delivery member, a cohesion of the substance causes the at least two interior opposing surfaces of the tunnel member to stick together increasing a force required to separate the at least two interior opposing surfaces and increasing a resistance to fluid flow through the tunnel lumen; and
   where the device body, tunnel member, and a portion of the fluid delivery conduit located within the tunnel member can be compressed to fit within an oral dosage form to allow ingestion or swallowing of the medical device.

17. The medical device of claim 16, where the fluid delivery member extends within the tunnel member such that the at least two interior opposing surfaces of the tunnel member hold the fluid delivery member in place by friction until withdrawn by pulling of the fluid delivery member.

18. The medical device of claim 16, wherein the substance comprises a viscous material.

19. The medical device of claim 16, further comprising at least one pocket in fluid communication with the tunnel lumen where the at least one pocket is configured to retain the substance therein.

* * * * *